United States Patent
Chatterjee et al.

(10) Patent No.: US 7,638,091 B2
(45) Date of Patent: Dec. 29, 2009

(54) METHODS OF STERILIZING POLYCARBONATE ARTICLES AND METHODS OF MANUFACTURE

(75) Inventors: Gautam Chatterjee, Bangalore (IN); Dibakar Dhara, Bangalore (IN); Katherine Glasgow, Evansville, IN (US); Antoinette van Bennekom, Hansweert (NL); Jos van den Bogerd, Sint Annaland (NL); Adam Zerda, Evansville, IN (US)

(73) Assignee: SABIC Innovative Plastics IP B. V., Bergen op Zoom (NL)

( * ) Notice: Subject to any disclaimer, the term of this patent is extended or adjusted under 35 U.S.C. 154(b) by 578 days.

(21) Appl. No.: 10/884,261

(22) Filed: Jul. 2, 2004

(65) Prior Publication Data
US 2006/0002814 A1    Jan. 5, 2006

(51) Int. Cl.
*A61L 2/08* (2006.01)
(52) U.S. Cl. .................................................. 422/26
(58) Field of Classification Search .............. 422/26
See application file for complete search history.

(56) References Cited

U.S. PATENT DOCUMENTS

| | | | |
|---|---|---|---|
| 3,169,121 A | 2/1965 | Goldberg | |
| 3,781,378 A * | 12/1973 | Kantor | 528/29 |
| 3,961,122 A | 6/1976 | Gaines, Jr. et al. | |
| 3,994,988 A * | 11/1976 | Laurin | 528/26 |
| 3,995,739 A | 12/1976 | Tasch et al. | |
| 4,000,341 A | 12/1976 | Matson | |
| 4,088,518 A | 5/1978 | Kehren et al. | |
| 4,217,438 A | 8/1980 | Brunelle et al. | |
| 4,238,597 A | 12/1980 | Markezich et al. | |
| 4,250,071 A | 2/1981 | Perrey et al. | |
| 4,287,108 A | 9/1981 | Grigo et al. | |
| 4,292,222 A | 9/1981 | Grigo et al. | |
| 4,305,856 A | 12/1981 | Sakano et al. | 260/29.1 SB |
| 4,322,465 A | 3/1982 | Webster | |
| 4,390,668 A | 6/1983 | Garver, Sr. | |
| 4,440,815 A | 4/1984 | Zomorodi et al. | |
| 4,453,940 A | 6/1984 | Aoyagi et al. | |
| 4,472,564 A | 9/1984 | Lockhart | |
| 4,487,896 A | 12/1984 | Mark et al. | |
| 4,569,970 A | 2/1986 | Paul et al. | |
| 4,600,632 A | 7/1986 | Paul et al. | |
| 4,681,922 A | 7/1987 | Schmidt et al. | |
| 4,746,701 A | 5/1988 | Kress et al. | |

(Continued)

FOREIGN PATENT DOCUMENTS

DE          40 16 417 A1     11/1991

(Continued)

OTHER PUBLICATIONS

International Search Report; International Application No. PCT/US2005/023500; Date of Mailing Jul. 26, 2006.

*Primary Examiner*—Sean Conley
*Assistant Examiner*—Kevin Joyner

(57) ABSTRACT

A method comprising treating an article with steam, wherein the article comprises a composition comprising an amount of a polysiloxane-polycarbonate copolymer effective to provide thermal and hydrolytic stability to the article for at least 15 cycles, wherein each cycle comprises 20 minutes of contact with steam at 100° C., at atmospheric pressure. The articles are of utility in a wide variety of applications such as food service and medical applications.

21 Claims, 3 Drawing Sheets

U.S. PATENT DOCUMENTS

| | | | |
|---|---|---|---|
| 4,748,166 A | 5/1988 | Gautier et al. | |
| 4,788,252 A | 11/1988 | de Boer et al. | |
| 4,849,490 A | 7/1989 | Barthelemy | |
| 4,898,956 A | 2/1990 | Hilty | |
| 4,975,190 A | 12/1990 | Sakashita et al. | |
| 5,023,297 A | 6/1991 | Boutni | |
| 5,075,351 A | 12/1991 | Joslyn et al. | |
| 5,109,076 A | 4/1992 | Freitag et al. | |
| 5,126,428 A | 6/1992 | Freitag et al. | |
| 5,246,979 A | 9/1993 | Lutz et al. | |
| 5,306,798 A | 4/1994 | Horn et al. | |
| 5,322,882 A | 6/1994 | Okamoto | |
| 5,326,834 A | 7/1994 | Sauers et al. | |
| 5,380,795 A | 1/1995 | Gosens et al. | |
| 5,391,603 A | 2/1995 | Wessel et al. | |
| 5,430,121 A | 7/1995 | Pudleiner et al. | |
| 5,451,632 A | 9/1995 | Okumura et al. | |
| 5,488,086 A | 1/1996 | Umeda et al. | |
| 5,521,258 A | 5/1996 | Cooper et al. | |
| 5,530,083 A | 6/1996 | Phelps et al. | |
| 5,597,887 A | 1/1997 | King, Jr. et al. | |
| 5,608,026 A | 3/1997 | Hoover et al. | |
| 5,616,674 A | 4/1997 | Michel et al. | |
| 5,741,566 A | 4/1998 | Hogstrom et al. | |
| 5,804,620 A | 9/1998 | Amos | |
| 6,001,929 A | 12/1999 | Nodera et al. | |
| 6,022,941 A | 2/2000 | Mestanza et al. | |
| 6,072,011 A | 6/2000 | Hoover | |
| 6,087,468 A | 7/2000 | Hoeks et al. | |
| 6,303,200 B1 | 10/2001 | Woo et al. | |
| 6,313,254 B1 | 11/2001 | Meijs et al. | |
| 6,559,270 B1 | 5/2003 | Siclovan et al. | |
| 6,576,706 B1 | 6/2003 | Nodera et al. | |
| 6,610,363 B2 | 8/2003 | Arora et al. | |
| 6,627,724 B2 | 9/2003 | Meijs et al. | |
| 6,657,018 B1 | 12/2003 | Hoover | 525/464 |
| 2002/0115795 A1 | 8/2002 | Shang et al. | |
| 2003/0092837 A1 | 5/2003 | Eichenauer | |
| 2003/0105226 A1 | 6/2003 | Cella et al. | |
| 2003/0119986 A1 | 6/2003 | Eichenauer | |
| 2004/0039145 A1 | 2/2004 | Silva et al. | |
| 2004/0220330 A1 | 11/2004 | DeRudder et al. | |
| 2005/0043816 A1* | 2/2005 | Datta et al. | 623/23.61 |

FOREIGN PATENT DOCUMENTS

| | | |
|---|---|---|
| EP | 0 248 308 A2 | 9/1987 |
| EP | 0 248 308 A2 | 12/1987 |
| EP | 0 254 054 B1 | 1/1988 |
| EP | 0 376 052 B1 | 7/1990 |
| EP | 0 387 570 B1 | 9/1990 |
| EP | 0 434 848 B1 | 7/1991 |
| EP | 0 524 731 | 6/1992 |
| EP | 0 517 927 B1 | 12/1992 |
| EP | 0 522 753 A2 | 1/1993 |
| EP | 0 600 196 | 10/1993 |
| EP | 0 645 422 A1 | 3/1995 |
| GB | 2 043 083 A | 10/1980 |
| JP | 04-225062 | 8/1992 |

* cited by examiner

◇ T-Exl  
□ 80% T-Exl+205 BHPM BPA PC  
△ 60% T-Exl+40% BHPM BPA PC  
✕ 40% T-Exl=60% BHPM BPA PC  
✱ 80% T-Exl+20% BHPM BPA PC  
○ 100% BHPM BPA PC

◇ T-Exl  
□ 80% T-Exl+20% BHPM BPA PC  
△ 60% T-Exl+40% BHPM BPA PC  
✕ 20% T-Exl+80% BHPM BPA PC  
○ BHPM BPA PC 100%

METHODS OF STERILIZING POLYCARBONATE ARTICLES AND METHODS OF MANUFACTURE

BACKGROUND OF THE INVENTION

This disclosure relates to polycarbonate articles, and in particular to polycarbonate articles that can be repeatedly sterilized and methods of manufacture thereof.

Polycarbonates are useful in the manufacture of articles and components for a wide range of applications, from automotive parts to medical devices. Because of their broad use, it is desirable to provide polycarbonates with improved thermal and hydrolytic stability. Medical devices in particular are desirably resistant to steam sterilization. Although some polycarbonate articles can be steam sterilized one time, the repeated steam sterilization of many polycarbonate articles generally results in a degradation of the advantageous physical and/or mechanical properties of polycarbonate.

Resistance to steam sterilization, for the most part, has been attempted by using materials that have higher glass transition temperatures and heat distortion temperatures. Some of these materials have been polyetherimides, polysulfones, Bayer APEC (a high heat polycarbonate) and polyphthalyl carbonate (PPC, a high heat copolyester polycarbonate). Generally though, these materials have drawbacks that prevent their widespread use in articles that are usually steam sterilized. For example, polyetherimides are colored, relatively expensive, and have low impact strength. Polysulfones color upon exposure to light, tend to be brittle, are viscous, and can absorb water. Bayer APEC is a stiff material that presents processing challenges and that can also be sensitive to hydrolysis, and certain copolyester polycarbonates tend to be brittle, colored materials. There accordingly remains a demand in the art for polycarbonate articles that do not exhibit significantly degraded physical and/or mechanical properties despite being repeatedly steam sterilized.

BRIEF DESCRIPTION OF THE INVENTION

The above-described and other deficiencies of the art are met by a method comprising treating an article with steam, wherein at least a portion of the article is formed from a composition comprising an amount of a polysiloxane-polycarbonate copolymer effective to provide thermal and hydrolytic stability to the article for at least 15 cycles, wherein each cycle comprises 20 minutes of contact with steam at 121° C. or greater, at 1.5 atmospheres or greater.

In yet another embodiment, a method for the manufacture of a thermally and hydrolytically resistant article comprises forming at least a portion of the article from a composition comprising an amount of a polysiloxane-polycarbonate copolymer effective to provide thermal and hydrolytic stability to the article for at least 15 cycles, wherein each cycle comprises 20 minutes of contact with steam at 121° C. or greater, at 1.5 atmospheres or greater.

In another embodiment there is provided an article that is formed by the above-described method.

In another embodiment, and article having improved resistance to steam sterilization comprises an amount of a polysiloxane-polycarbonate copolymer effective to provide thermal and hydrolytic stability to the article for at least 15 cycles, wherein each cycle comprises 20 minutes of contact with steam at 121° C. or greater, at 1.5 atmospheres or greater.

DETAILED DESCRIPTION OF THE INVENTION

Figure 1:
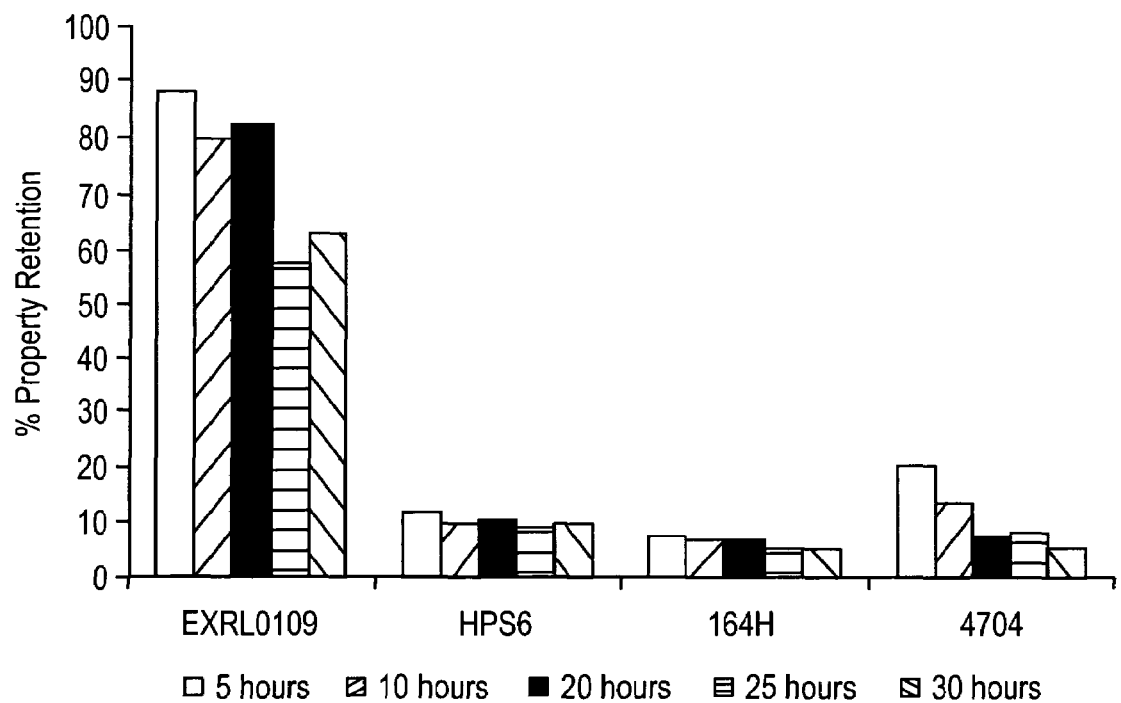
FIG. 1 shows a comparison of the notched Izod impact retention for selected polycarbonate compositions after steam treatment.

It has been unexpectedly discovered by the inventors hereof that polysiloxane polycarbonate copolymers can be used to provide articles with improved resistance to thermal and hydrolytic degradation. In a particularly advantageous feature, it has been found that such articles can be repeatedly treated with steam (for example, steam sterilized) without significant degradation of at least one advantageous property. In one embodiment, it has been found that the articles, despite repeated treatment with heat and/or steam, show little to no impairment in dimensional stability, ductility, impact strength, transparency, and/or Vicat softening temperature.

In order to impart adequate heat resistance during treatment with heat and/or steam, for example steam sterilization, the articles are formed from compositions comprising a polysiloxane-polycarbonate copolymer. Such copolymers comprise polysiloxane blocks and polycarbonate blocks. The polycarbonate block comprise repeating structural carbonate units of the formula (1):

(1)

in which at least 60 percent of the total number of $R^1$ groups are aromatic organic radicals and the balance thereof are aliphatic, alicyclic, or aromatic radicals. Each $R^1$ can be an aromatic organic radical and, can be a radical of the formula (2):

$-A^1-Y^1-A^2-$ (2)

wherein each of $A^1$ and $A^2$ is a monocyclic divalent aryl radical and $Y^1$ is a bridging radical having one or two atoms that separate $A^1$ from $A^2$. In an exemplary embodiment, one atom separates $A^1$ from $A^2$. Illustrative non-limiting examples of radicals of this type are —O—, —S—, —S(O)—, —S(O$_2$)—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ can be a hydrocarbon group or a saturated hydrocarbon group such as methylene, cyclohexylidene, or isopropylidene.

Polycarbonate units can be produced by the interfacial or melt reaction of dihydroxy compounds having the formula HO—R¹—OH, which includes dihydroxy compounds of formula (3)

  (3)

wherein $Y^1$, $A^1$ and $A^2$ are as described above. Also included are bisphenol compounds of general formula (4):

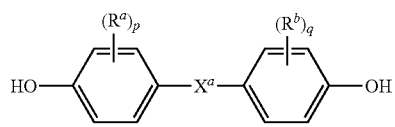  (4)

wherein $R^a$ and $R^b$ each represent a halogen atom or a monovalent hydrocarbon group and can be the same or different; p and q are each independently integers of 0 to 4; and $X^a$ represents one of the groups of formula (5):

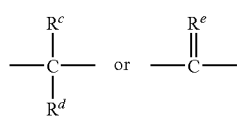  (5)

wherein $R^c$ and $R^d$ each independently represent a hydrogen atom or a monovalent linear or cyclic hydrocarbon group and $R^e$ is a divalent hydrocarbon group.

Some illustrative, non-limiting examples of suitable dihydroxy compounds include the dihydroxy-substituted hydrocarbons disclosed by name or formula (generic or specific) in U.S. Pat. No. 4,217,438. A nonexclusive list of specific examples of suitable dihydroxy compounds includes the following: resorcinol, 4-bromoresorcinol, hydroquinone, 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis (hydroxyphenyl)cyclopentane, 1, 1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantine, (alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl) propane, 2,2-bis(4-hydroxyphenyl)hexafluoropropane, 1, 1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis (4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis (4-hydroxyphenyl)sulfone, 9,9-bis(4-hydroxyphenyl) fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, and the like, as well as mixtures comprising the foregoing dihydroxy compounds.

A nonexclusive list of specific examples of the types of bisphenol compounds that can be represented by formula (3) includes 1,1-bis(4-hydroxyphenyl)methane, 1,1-bis(4-hydroxyphenyl)ethane, 2,2-bis(4-hydroxyphenyl)propane (hereinafter "bisphenol A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-1-methylphenyl)propane, and 1,1-bis(4-hydroxy-t-butylphenyl)propane. Combinations comprising the foregoing dihydroxy compounds can also be used.

Branched polysiloxane-polycarbonate copolymer may also be useful, as well as blends comprising linear polycarbonate units and branched polycarbonate units. The branched polycarbonate units can be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris ((p-hydroxyphenyl)isopropyl)benzene), tris-phenol PA (4(4 (1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents can be added at a level of 0.05 to 2.0 weight percent (wt. %). All types of polycarbonate end groups are contemplated as being useful in the polycarbonate composition.

"Polycarbonate units" as used herein further includes copolymers comprising carbonate chain units and other chain units. A specific suitable copolymeric unit is a polyester carbonate unit, also known as a copolyester polycarbonate unit. Such copolymer units further contain, in addition to recurring carbonate chain units of the formula (1), repeating units of formula (6)

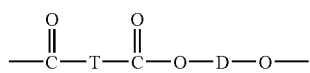  (6)

wherein D is a divalent radical derived from a dihydroxy compound, and can be, for example, a $C_{2-10}$ alkylene radical, a $C_{6-20}$ alicyclic radical, a $C_{6-20}$ aromatic radical or a polyoxyalkylene radical in which the alkylene groups contain 2 to 6 carbon atoms, which can be 2, 3, or 4 carbon atoms; and T divalent radical derived from a dicarboxylic acid, and can be, for example, a $C_2$-10 alkylene radical, a $C_{6-20}$ alicyclic radical, a $C_{6-20}$ alkyl aromatic radical, or a $C_{6-20}$ aromatic radical.

In one embodiment, D is a $C_{2-6}$ alkylene radical. In another embodiment, D is derived from an aromatic dihydroxy compound of formula (7):

(7)

wherein each $R^f$ is independently a halogen atom, a $C_{1-10}$ hydrocarbon group, or a $C_{1-10}$ halogen substituted hydrocarbon group, and n is 0 to 4. The halogen can be bromine. Examples of compounds that can be represented by the formula (7) include resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluororesorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluorohydroquinone, 2,3,5,6-tetrabromo hydroquinone, or the like; or combinations comprising at least one of the foregoing compounds.

Examples of aromatic dicarboxylic acids that can be used to prepare the polyesters include isophthalic or terephthalic acid, 1,2-di(p-carboxyphenyl)ethane, 4,4'-dicarboxydiphenyl ether, 4,4'-bisbenzoic acid, and mixtures comprising at least one of the foregoing acids. Acids containing fused rings can also be present, such as in 1,4-, 1,5-, or 2,6-naphthalenedicarboxylic acids. The specific dicarboxylic acids are terephthalic acid, isophthalic acid, naphthalene dicarboxylic acid, cyclohexane dicarboxylic acid, or combinations comprising at least one of the foregoing dicarboxylic acids. A specific dicarboxylic acid comprises a mixture of isophthalic acid and terephthalic acid wherein the weight ratio of terephthalic acid to isophthalic acid is 10:1 to 0.2:9.8. In another specific embodiment, D is a $C_{2-6}$ alkylene radical and T is p-phenylene, m-phenylene, naphthalene, a divalent cycloaliphatic radical, or a mixture thereof. This class of polyester includes the poly(alkylene terephthalates).

In addition to the repeating structural carbonate units (1), the copolymers comprise polydiorganosiloxane blocks comprising repeating structural units of formula (8):

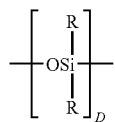

(8)

wherein each occurrence of R is same or different, and is a $C_{1-13}$ monovalent organic radical. For example, R may be a $C_1$-$C_{13}$ alkyl group, $C_1$-$C_{13}$ alkoxy group, $C_2$-$C_{13}$ alkenyl group, $C_2$-$C_{13}$ alkenyloxy group, $C_3$-$C_6$ cycloalkyl group, $C_3$-$C_6$ cycloalkoxy group, $C_6$-$C_{10}$ aryl group, $C_6$-$C_{10}$ aryloxy group, $C_7$-$C_{13}$ aralkyl group, $C_7$-$C_{13}$ aralkoxy group, $C_7$-$C_{13}$ alkaryl group, or $C_7$-$C_{13}$ alkaryloxy group. Combinations of the foregoing R groups may be used in the same copolymer.

D in formula (8) is selected so as to provide an effective level of hydrolytic stability during repeated treatment with steam such as in steam sterilization cycles. The value of D will therefore vary depending on the type and relative amount of each component in the composition, including the type and amount of polycarbonate blocks, the type an amount of any polycarbonate resin as described below (if present), the type and amount of any impact modifier (if present), the type polysiloxane units, and the type and amount of any other additives present in the composition. Suitable values for D may be determined by one of ordinary skill in the art without undue experimentation using the guidelines taught herein. Generally, D has an average value of 2 to 1000, specifically 10 to 100, more specifically 25 to 75. In one embodiment, D has an average value of 40 to 60, and in still another embodiment, D has an average value of 50. Where D is of a lower value, e.g., less than 40, it may be allowable or advantageous to use a relatively larger amount of the polysiloxane-polycarbonate copolymer. Conversely, where D is of a higher value, e.g., greater than 40, it may be allowable or advantageous to use a relatively smaller amount of the polysiloxane-polycarbonate copolymer.

Specific polysiloxane-polycarbonate copolymers will be selected by those skilled in the art so as not to impair the properties of thermal and hydrolytic stability of articles manufactured from the composition. A specific type of suitable polysiloxane-polycarbonate copolymer has polydiorganosiloxane blocks comprising repeating structural units of formula (9):

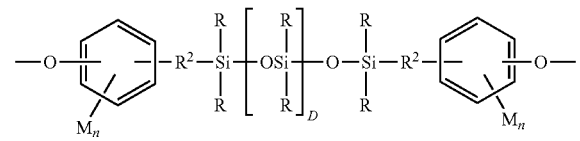

(9)

wherein D is as described above, and each occurrence of R is same or different, and is a $C_{1-13}$ monovalent organic radical. For example, R can be a $C_1$-$C_{13}$ alkyl group, $C_1$-$C_{13}$ alkoxy group, $C_2$-$C_{13}$ alkenyl group, $C_2$-$C_{13}$ alkenyloxy group, $C_3$-$C_6$ cycloalkyl group, $C_3$-$C_6$ cycloalkoxy group, $C_6$-$C_{10}$ aryl group, $C_6$-$C_{10}$ aryloxy group, $C_7$-$C_{13}$ aralkyl group, $C_7$-$C_{13}$ aralkoxy group, $C_7$-$C_{13}$ alkaryl group, or $C_7$-$C_{13}$ alkaryloxy group. Combinations of the foregoing R groups can be used in the same copolymer. $R^2$ in formula (6) is a divalent $C_1$-$C_8$ aliphatic group. Each M in formula (9) can be the same or different, and can be a halogen, cyano, nitro, $C_1$-$C_8$ alkylthio, $C_1$-$C_8$ alkyl, $C_1$-$C_8$ alkoxy, $C_2$-$C_8$ alkenyl, $C_2$-$C_8$ alkenyloxy group, $C_3$-$C_8$ cycloalkyl, $C_3$-$C_8$ cycloalkoxy, $C_6$-$C_{10}$ aryl, $C_6$-$C_{10}$ aryloxy, $C_7$-$C_{12}$ aralkyl, $C_7$-$C_{12}$ aralkoxy, $C_7$-$C_{12}$ alkaryl, or $C_7$-$C_{12}$ alkaryloxy, wherein each n is independently 0, 1, 2, 3, or 4.

In one embodiment, M is independently bromo or chloro, a $C_1$-$C_3$ alkyl group such as methyl, ethyl, or propyl, a $C_1$-$C_3$ alkoxy group such as methoxy, ethoxy, or propoxy, or a $C_6$-$C_7$ aryl group such as phenyl, chlorophenyl, or tolyl; $R^2$ is a dimethylene, trimethylene or tetramethylene group; and R is a $C_{1-8}$ alkyl, haloalkyl such as trifluoropropyl, cyanoalkyl, or aryl such as phenyl, chlorophenyl or tolyl. In another embodiment, R is methyl, or a mixture of methyl and trifluoropropyl, or a mixture of methyl and phenyl. In still another embodiment, M is methoxy, n is one, $R^2$ is a divalent $C_1$-$C_3$ aliphatic group, and R is methyl.

These units can be derived from the corresponding dihydroxy polydiorganosiloxane (10):

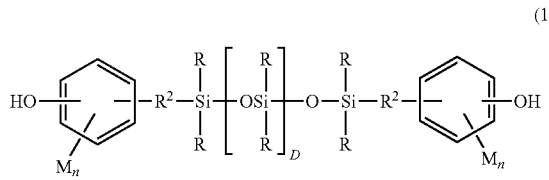

wherein Y, R, D, M, $R^2$, and n are as described above. Such dihydroxy polysiloxanes can be made by effecting a platinum catalyzed addition of a siloxane hydride of the formula (11):

wherein R and D are as previously defined, with an aliphatically unsaturated monohydric phenol. Suitable aliphatically unsaturated monohydric phenols include, for example, eugenol, 2-alkylphenol, 4-allyl-2-methylphenol, 4-allyl-2-phenylphenol, 4-allyl-2-bromophenol, 4-allyl-2-t-butoxyphenol, 4-phenyl-2-phenylphenol, 2-methyl-4-propylphenol, 2-allyl-4,6-dimethylphenol, 2-allyl-4-bromo-6-methylphenol, 2-allyl-6-methoxy-4-methylphenol and 2-allyl-4,6-dimethylphenol. Mixtures comprising the foregoing aliphatically unsaturated monohydric phenols can also be used.

The polysiloxane-polycarbonate copolymer can be manufactured by reaction of dihydroxy polysiloxane (10) with a carbonate source and a dihydroxy aromatic compound of formula (3) by processes such as interfacial polymerization and melt polymerization. Although the reaction conditions for interfacial polymerization can vary, an exemplary process generally involves dissolving or dispersing the dihydric reactants in aqueous caustic soda or potash, adding the resulting mixture to a suitable water-immiscible solvent medium, and contacting the reactants with a carbonate precursor in the presence of a suitable catalyst such as triethylamine or a phase transfer catalyst, and under controlled pH conditions, e.g., 8-10. In one embodiment, the copolymers are be prepared by phosgenation, at temperatures of below 0° C. to 100° C., and can further be prepared at temperatures of 25° C. to 50° C. The most commonly used water immiscible solvents include methylene chloride, 1,2-dichloroethane, chlorobenzene, toluene, and the like. Suitable carbonate precursors include, for example, a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In one embodiment, a monofunctional compound such as a phenol, tert-butyl phenol or para-cumylphenol, may be present to function as a chain termination agent to limit the molecular weight of the polycarbonate.

Among the specific phase transfer catalysts that can be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-188}$ aryloxy group. Suitable phase transfer catalysts include, for example, $[CH_3(CH_2)_3]_4NX$, $[CH_3(CH_2)_4]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, $CH_3[CH_3(CH_2)_2]_3NX$ wherein X is $Cl^-$, $Br^-$, or a $C_{1-8}$ alkoxy group or $C_{6-188}$ aryloxy group. An effective amount of a phase transfer catalyst can be 0.1 to 10 wt. % based on the weight of dihydric reactant in the phosgenation mixture. In another embodiment an effective amount of phase transfer catalyst can be 0.5 to 2 wt. % based on the weight of bisphenol in the phosgenation mixture. One or both of the tube reactor processes described in U.S. Patent Application No. 2004/0039145A1 may be used to synthesize the polysiloxane-polycarbonate copolymers.

Alternatively, melt processes can be used to make the copolymers. Generally, in the melt polymerization process, the copolymers can be prepared by co-reacting, in a molten state, the dihydroxy reactants and a diaryl carbonate ester, such as diphenyl carbonate, in the presence of a transesterification catalyst in a Banbury mixer, twin screw extruder, or the like to form a uniform dispersion. Volatile monohydric phenol is removed from the molten reactants by distillation and the polymer is isolated as a molten residue.

The polycarbonate copolymers comprising polyester units may also be prepared by interfacial polymerization techniques, such as is described, for example, in U.S. Pat. Nos. 3,169,121 and 4,487,896. Rather than utilizing the dicarboxylic acid per se, it is possible, and can sometimes be even preferred, to employ the reactive derivatives of the acid, such as the corresponding acid halides, in particular the acid dichlorides and the acid dibromides. Thus, for example instead of using isophthalic acid, terephthalic acid or mixtures thereof, it is possible to employ isophthaloyl dichloride, terephthaloyl dichloride, and combinations comprising at least one of the foregoing.

In the production of the polysiloxane-polycarbonate copolymer, the amount of dihydroxy polydiorganosiloxane is selected so as to provide an effective level of hydrolytic resistance to the composition upon repeated exposure to steam. The amount of dihydroxy polydiorganosiloxane will therefore vary depending on the value of D, the relative amount and type of each component in the composition, including the polycarbonate blocks, the polysiloxane blocks, any polycarbonate resin, any impact modifier, and any other additives. Suitable values for the amount of dihydroxy polydiorganosiloxane can be determined by one of ordinary skill in the art without undue experimentation using the guidelines taught herein. Typically, the amount of dihydroxy polydiorganosiloxane is selected so as to produce a copolymer comprising 0.1 to 40 wt. % of polydimethylsiloxane, or an equivalent molar amount of another polydiorganosiloxane. This copolymer can then be combined with other polymers to make blends, including blends comprising polysiloxane-polycarbonate copolymers that have different polysiloxane contents. When less than 0.1 wt. % of polydimethylsiloxane units are present, adequate heat resistance is not achieved, even if higher amounts of the copolymer are present in the composition. Greater than 40 wt. % polydimethylsiloxane units may adversely affect physical properties of the composition, such as delamination in molded products, lower heat deformation temperatures, and difficulty in processing.

In a typical embodiment, the amount of dihydroxy polydiorganosiloxane is selected so as to produce a copolymer comprising 0.5 to 12 wt. % of polydimethylsiloxane, or an equivalent molar amount of another polydiorganosiloxane. In another embodiment, the amount of dihydroxy polydiorganosiloxane is selected so as to produce a copolymer comprising 1 to 7 wt. % of polydimethylsiloxane, or an equivalent molar amount of another polydiorganosiloxane. These copolymers can be used to produce either opaque or transparent articles, depending on how the copolymers were synthesized, as is described in the art.

The polysiloxane-polycarbonate copolymers can have a weight-average molecular weight (MW, measured, for example, by gel permeation chromatography, ultra-centrifugation, or light scattering) of 10,000 to 200,000, specifically 20,000 to 100,000. In general, the polysiloxane-polycarbonate copolymers can have a weight-average molecular weight of 15,000 to 100,000. Suitable polysiloxane-polycarbonate copolymers are commercially available from GE Plastics.

In addition to a polysiloxane polycarbonate copolymer as described above, the compositions may comprise one or more additional components, for example an additional thermoplastic resins and/or fillers and other additives. The additional component(s) are selected so as to not significantly adversely affect the thermal and hydrolytic stability of the composition, and may therefore be high heat materials.

In one embodiment the composition comprises a high heat thermoplastic polymer that does not significantly adversely affect the desirable properties of the composition before or after treatment with steam as described in more detail below. In one embodiment a high heat thermoplastic polymer has a heat deflection temperature (HDT) at 1.8 Megapascals (MPa) of greater than 135° C. In another embodiment, a high heat thermoplastic polymer has a heat deflection temperature at 0.45 MPa of greater than 150° C. Heat deflection temperature may be measured in accordance with ASTM 648.

The high heat thermoplastic polymer may be selected from the group consisting of polyoxymethylenes, polyarylates, polyether ether ketones, polyethersulfones, poly(ethylene terephthalate)s, polyphenylene sulfides, polycarbonates, and combinations comprising at least one of the foregoing high heat thermoplastic polymers.

In one embodiment, the high heat thermoplastic polymer can be a high heat polycarbonate comprising carbonate units of formula (1). A variety of high heat polycarbonates can be used and can be chosen by those skilled in the art so as to not impair the above-noted properties. In one embodiment, the high heat polycarbonate is a copolymer comprising units derived from a dihydroxy compound of formula (3), preferably a bisphenol compound of formula (4), together with units derived from a high heat monomer. Suitable high heat monomers include, for example, bis(4-hydroxyphenyl)-p-menthane, 2-phenyl-3-3-bis(4-hydroxylphenyl) phthalimidine (PPP), 4,4'-(hexahydro-4,7-methano-indan-5-ylidene) diphenol (TCD, or tricyclodecane bisphenol), bisphenol TMC (1,3,5-trimethylcyclohexane) (as found in Bayer's APEC material), 4-[1-[3-(4-hydroxyphenyl)-4-methylcyclohexyl]-1-methylethyl] phenol, 4,4'-[1-methyl-4-(1-methylethyl)-1,3-cyclohexandiyl]bisphenol, phenolphthalein, 2-methyl-3,3-bis(p-hydroxyphenyl)phthalimide, 2-butyl-3,3-bis(p-hydroxyphenyl)phthalimide, 2-octyl-3,3-bis(p-hydroxyphenyl)phthalimide, and 1,3-bis(4-hydroxyphenyl)-1,3-dialkylcyclohexane wherein the alkyl groups have one to four carbon atoms, as described, for example, in U.S. Pat. No. 5,344,999. Specific examples of suitable high heat polycarbonates comprises units derived from the foregoing high heat monomers together with monomers derived from 1,1-bis(4-hydroxyphenyl)methane, 1,1-bis(4-hydroxyphenyl)ethane, bisphenol A, 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-1-methylphenyl)propane, and 1,1-bis(4-hydroxy-t-butylphenyl) propane. Alternatively, the high heat polycarbonate can be made from the foregoing polycarbonate monomers, which are then blended with the high heat monomer or other polymers that provide high heat resistance.

Another suitable high heat polycarbonate is a copolyester polycarbonate comprising units of formula (1) together with polyester units of formula (6). Again, the units of formula (1) may be derived from high heat dihydric compounds such as bis(4-hydroxyphenyl)-p-menthane, or a combination of high heat dihydric compounds and other dihydric compounds such as Bisphenol A. The ester units are preferably aromatic. In one embodiment, the ester units are derived from aromatic dicarboxylic acids such as isophthalic or terephthalic acid.

The average molecular weight of the high heat polycarbonate may be 5,000 to 100,000, more specifically 10,000 to 65,000, and most specifically 15,000 to 45,000 as measured by gel permeation chromatography. Mixtures of polycarbonates of different weights can be used to achieve the desired viscosity and/or other physical properties.

The high heat polycarbonates can be manufactured by processes such as interfacial polymerization and melt polymerization as described above. Suitable procedures for the manufacture of high heat copolyester polycarbonates are set forth, for example, in U.S. Pat. No. 4,238,597. Suitable high heat polycarbonates are commercially available under the trade names LEXAN 4704, 4504, and 4404 available from GE Plastics; and APEC available from Bayer.

In addition to the high heat polycarbonate resins described above, it is also possible to use combinations of the polycarbonate resins with other thermoplastic polymers, for example combinations of polycarbonates and/or polycarbonate copolymers with polyesters. As used, a "combination" is inclusive of mixtures, blends, alloys, copolymers, and the like. Suitable polyesters comprise repeating units of formula (6), and can be, for example, poly(alkylene dicarboxylates), liquid crystalline polyesters, and polyester copolymers. It is also possible to use a branched polyester in which a branching agent, for example, a glycol having three or more hydroxyl groups or a trifunctional or multifunctional carboxylic acid had been incorporated. Furthermore, it is sometimes desirable to have various concentrations of acid and hydroxyl end groups on the polyester, depending on the ultimate end-use of the composition.

In one embodiment, poly(alkylene terephthalates) are used. Specific examples of suitable poly(alkylene terephthalates) are poly(ethylene terephthalate) (PET), poly(1,4-butylene terephthalate) (PBT), poly(ethylene naphthanoate) (PEN), poly(butylene naphthanoate), (PBN), (polypropylene terephthalate) (PPT), polycyclohexanedimethanol terephthalate (PCT), and combinations comprising at least one of the foregoing polyesters. Also contemplated are the above polyesters with a minor amount, e.g., from 0.5 to 10 percent by weight, of units derived from an aliphatic diacid and/or an aliphatic polyol to make copolyesters.

The blends of a polycarbonate and a polyester comprise 10 to 90 wt. % polycarbonate and correspondingly 90 to 10 wt. % polyester, in particular a poly(alkylene terephthalate). In one embodiment, the blend comprises 30 to 70 wt. % polycarbonate and correspondingly 70 to 30 wt. % polyester. The foregoing amounts are base on the total weight of the polycarbonate resin and polyester resin.

The composition can further include an impact modifier composition comprising a particular combination of impact modifiers to increase its impact resistance. Suitable impact modifiers can be an elastomer-modified graft copolymer comprising (i) an elastomeric (i.e., rubbery) polymer substrate having a Tg below 0° C., more specifically −40° to −80°

C., and (ii) a rigid polymeric superstrate grafted to the elastomeric polymer substrate. As is known, elastomer-modified graft copolymers can be prepared by first providing an elastomeric polymeric backbone. At least one grafting monomer, and specifically two, are then polymerized in the presence of the polymer backbone to obtain the graft copolymer.

Depending on the amount of elastomer-modified polymer present, a separate matrix or continuous phase of ungrafted rigid polymer or copolymer can be simultaneously obtained along with the elastomer-modified graft copolymer. Generally, such impact modifiers comprise 40 to 95 wt. % elastomer-modified graft copolymer and 5 to 60 wt. % graft (co)polymer, based on the total weight of the impact modifier. In another embodiment, such impact modifiers can comprise 50 to 85 wt. %, or can comprise 75 to 85 wt. % rubber-modified graft copolymer, together with 15 to 50 wt. %, more specifically 15 to 25 wt. % graft (co)polymer, based on the total weight of the impact modifier. The ungrafted rigid polymers or copolymers can also be separately prepared, for example by radical polymerization, in particular by emulsion, suspension, solution or bulk polymerization, and added to the impact modifier composition or polycarbonate composition. Such ungrafted rigid polymers or copolymers can have number average molecular weights of 20,000 to 200,000.

Suitable materials for use as the elastomeric polymer backbone include, for example, conjugated diene rubbers; copolymers of a conjugated diene with less than 50 wt. % of a copolymerizable monomer; $C_{1-8}$ alkyl (meth)acrylate elastomers; olefin rubbers such as ethylene propylene copolymers (EPR) or ethylene-propylene-diene monomers (EPDM); silicone rubbers; elastomeric $C_{1-8}$ alkyl (meth)acrylates; elastomeric copolymers of $C_{1-8}$ alkyl (meth)acrylates with butadiene and/or styrene; or combinations comprising at least one of the foregoing elastomers.

Suitable conjugated diene monomers for preparing the polymeric backbone are of formula (12):

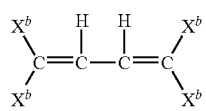

(12)

where each $X^b$ is independently hydrogen, $C_1$-$C_5$ alkyl, chlorine, bromine, or the like. Examples of conjugated diene monomers that can be used are butadiene, isoprene, 1,3-heptadiene, methyl-1,3-pentadiene, 2,3-dimethyl-1,3-butadiene, 2-ethyl-1,3-pentadiene; 1,3- and 2,4-hexadienes, chloro- and bromo-substituted butadienes such as dichlorobutadiene, bromobutadiene, dibromobutadiene, and the like, as well as mixtures comprising at least one of the foregoing conjugated diene monomers. Specific conjugated diene homopolymers include polybutadiene and polyisoprene.

Copolymers of a conjugated diene rubber can also be used, for example those produced by aqueous radical emulsion polymerization of a conjugated diene and one or more monomers copolymerizable therewith. Monomers that are suitable for copolymerization with the conjugated diene include monovinylaromatic monomers containing condensed aromatic ring structures, such as vinyl naphthalene, vinyl anthracene and the like, or monomers of formula (13):

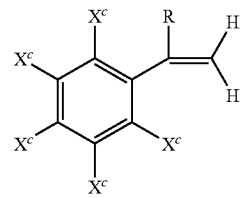

(13)

where each $X^c$ is independently hydrogen, $C_1$-$C_{12}$ alkyl, $C_3$-$C_{12}$ cycloalkyl, $C_6$-$C_{12}$ aryl, $C_7$-$C_{12}$ aralkyl, $C_7$-$C_{12}$ alkaryl, $C_1$-$C_{12}$ alkoxy, $C_3$-$C_{12}$ cycloalkoxy, $C_6$-$C_{12}$ aryloxy, chloro, bromo, or hydroxy, and R is hydrogen, $C_1$-$C_5$ alkyl, bromo, or chloro. Examples of the suitable monovinylaromatic monomers that can be used include styrene, 3-methylstyrene, 3,5-diethylstyrene, 4-n-propylstyrene, alpha-methylstyrene, alpha-methyl vinyltoluene, alpha-chlorostyrene, alpha-bromostyrene, dichlorostyrene, dibromostyrene, tetrachlorostyrene, combinations comprising at least one of the foregoing compounds, and the like. Styrene and/or alpha-methylstyrene are commonly used as monomers copolymerizable with the conjugated diene monomer. Mixtures of the foregoing monovinyl monomers and monovinylaromatic monomers can also be used.

Other monomers that can be copolymerized with the conjugated diene are monovinylic monomers such as itaconic acid, acrylamide, N-substituted acrylamide or methacrylamide, maleic anhydride, maleimide, N-alkyl, aryl or haloaryl substituted maleimide, glycidyl (meth)acrylates, and monomers of the general formula (14):

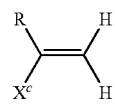

(14)

where R is as previously defined and $X^c$ is cyano, $C_1$-$C_{12}$ alkoxycarbonyl, $C_1$-$C_{12}$ aryloxycarbonyl, or the like. Examples of monomers of formula (XV) include acrylonitrile, ethacrylonitrile, methacrylonitrile, alpha-chloroacrylonitrile, beta-chloroacrylonitrile, alpha-bromoacrylonitrile, methyl acrylate, methyl methacrylate, ethyl acrylate, n-butyl acrylate, n-butyl methacrylate, propyl acrylate, isopropyl acrylate, 2-ethylhexyl acrylate, combinations comprising at least one of the foregoing monomers, and the like. Monomers such as n-butyl acrylate, ethyl acrylate, and 2-ethylhexyl acrylate are commonly used as monomers copolymerizable with the conjugated diene monomer.

Suitable (meth)acrylate rubbers suitable for use as the elastomeric polymer backbone can be cross-linked, particulate emulsion homopolymers or copolymers of $C_{1-8}$ alkyl (meth)acrylates, in particular $C_{4-6}$ alkyl acrylates, optionally in admixture with up to 15 wt. % of comonomers such as styrene, methyl methacrylate, butadiene, isoprene, vinyl methyl ether or acrylonitrile, and mixtures comprising at least one of the foregoing comonomers. Optionally, up to 5 wt. % a polyfunctional crosslinking comonomer can be present, for example divinylbenzene, alkylenediol di(meth)acrylates such as glycol bisacrylate, alkylenetriol tri(meth)acrylates, polyester di(meth)acrylates, bisacrylamides, triallyl cyanurate, triallyl isocyanurate, allyl (meth)acrylate, diallyl maleate, diallyl fumarate, diallyl adipate, triallyl esters of citric acid, triallyl esters of phosphoric acid, and the like, as well as combinations comprising at least one of the foregoing crosslinking agents.

The elastomeric polymer substrate can be in the form of either a block or random copolymer. The particle size of the substrate is not critical, for example, the particle size of the substrate can be an average particle size of 0.05 to 1.2 micrometers, or can be 0.2 to 0.8 micrometers, for emulsion based polymerized rubber lattices or still further can be 0.5 to 10 micrometers, and still even further can be 0.6 to 1.5 micrometers, for mass polymerized rubber substrates which also have included grafted monomer occlusions. Particle size can be measured by simple light transmission methods or capillary hydrodynamic chromatography (CHDF). The rubber substrate can be a particulate, moderately cross-linked conjugated diene or $C_{4-6}$ alkyl acrylate rubber, and can have a gel content greater than 70%. Also suitable are mixtures of conjugated diene and $C_{4-6}$ alkyl acrylate rubbers.

In the preparation the elastomeric graft copolymer, the elastomeric polymer backbone can comprise 40 to 95 wt. % of the total graft copolymer, or can comprise 50 to 85 wt. %, and still further can comprise 75 to 85 wt. % of the elastomer-modified graft copolymer, the remainder being the rigid graft phase.

In one embodiment, the elastomer-modified graft polymer can be obtained by graft polymerization of a mixture comprising a monovinylaromatic monomer and optionally one or more comonomers in the presence of one or more elastomeric polymer substrates. The above-described monovinylaromatic monomers can be used in the rigid graft phase, including styrene, alpha-methyl styrene, halostyrenes such as dibromostyrene, vinyltoluene, vinylxylene, butylstyrene, para-hydroxystyrene, methoxystyrene, or combinations comprising at least one of the foregoing monovinylaromatic monomers. The monovinylaromatic monomers can be used in combination with one or more comonomers, for example the above-described monovinylic monomers and/or monomers of the general formula (XV). In one specific embodiment, the monovinylaromatic monomer is styrene or alpha-methyl styrene, and the comonomer is acrylonitrile, ethyl acrylate, and/or methyl methacrylate. In another specific embodiment, the rigid graft phase can be a copolymer of styrene and acrylonitrile, a copolymer of alpha-methylstyrene and acrylonitrile, or a methyl methacrylate homopolymer or copolymer.

Specific examples of such elastomer-modified graft copolymers include but are not limited to acrylonitrile-butadiene-styrene (ABS), acrylonitrile-styrene-butyl acrylate (ASA), methyl methacrylate-acrylonitrile-butadiene-styrene (MABS), and methyl methacrylate-butadiene-styrene (MBS), and acrylonitrile-ethylene-propylene-diene-styrene (AES).

In another embodiment, the elastomer-modified graft polymer can be obtained by emulsion graft polymerization of a mixture comprising one or more of the above-described monovinylic monomers and/or monomers of the general formula (XV) in the presence of one or more elastomeric polymer substrates. In one specific embodiment, the monovinylic monomer is acrylonitrile, methacrylonitrile, ethyl acrylate, methyl acrylate, and/or methyl methacrylate.

The elastomer-modified graft polymers can be polymerized by mass, emulsion, suspension, solution or combined processes such as bulk-suspension, emulsion-bulk, bulk-solution or other techniques, using continuous, semibatch, or batch processes. As described above, use of a particular combination of specific impact modifiers has led to surprisingly good results.

In particular, a first impact modifier is prepared by emulsion polymerization and is free of basic materials such as alkali metal salts of $C_{6-30}$ fatty acids, for example sodium stearate, lithium stearate, sodium oleate, potassium oleate, and the like, alkali metal carbonates, amines such as dodecyl dimethyl amine, dodecyl amine, and the like, and ammonium salts of amines. Such materials are commonly used as surfactants in emulsion polymerization, and can catalyze transesterification and/or degradation of polycarbonates. Instead, ionic sulfate, sulfonate, or phosphate surfactants can be used in preparing the impact modifiers, particularly the elastomeric substrate portion of the impact modifiers. Suitable surfactants include, for example, $C_{1-22}$ alkyl or $C_{7-25}$ alkylaryl sulfonates, $C_{1-22}$ alkyl or $C_{7-25}$ alkylaryl sulfates, $C_{1-22}$ alkyl or $C_{7-25}$ alkylaryl phosphates, substituted silicates, and combinations comprising at least one of the foregoing surfactants. A specific surfactant can be a $C_{6-16}$, and can further be a $C_{8-12}$ alkyl sulfonate.

The emulsion polymerization process for preparing the impact modifier of this invention is not critical and is described and disclosed in various patents and literature of such companies as Rohm & Haas and General Electric Company. In the practice, many of the above-described impact modifiers can be used providing it is free of the alkali metal salts of fatty acids, alkali metal carbonates, and other basic materials. In one embodiment, however, the impact modifier has a core-shell structure where the core is an elastomeric polymer substrate and the shell is a rigid thermoplastic polymer that is readily wet by the PC. The shell can merely physically encapsulate the core, or the shell can be partially or essentially completely grafted to the core. The shell can comprise the polymerization product of a monovinylaromatic compound and/or a monovinylic monomer or an alkyl (meth) acrylate. A specific impact modifier of this type is an MBS impact modifier where the butadiene substrate is prepared using above-described sulfonates, sulfates, or phosphates as surfactants. It is also preferred that the impact modifier have a pH of 3 to 8, or more preferably 4 to 7.

Acrylonitrile-butadiene-styrene graft copolymers are well known in the art and many are commercially available, including, for example, the high-rubber acrylonitrile-butadiene-styrene resins available from General Electric Company as BLENDEX® grades 131, 336, 338, 360, and 415.

In addition to the polycarbonate-polysiloxane copolymer, additional thermoplastic polymer, and any impact modifier (hereinafter "the resin composition"), the composition can include various additives ordinarily incorporated into compositions of this type, with the proviso that the additives do not adversely affect the desired properties of the composition, in particular hydrolytic and/or thermal stability after repeated treatment with steam. Thus, additives that generate degradation catalysts in the presence of moisture, for example hydrolytically unstable phosphites, would not be as desirable. Mixtures of additives can be used. Such additives can be mixed at a suitable time during the mixing of the components for forming the composition, or added in the form of a masterbatch.

Suitable fillers or reinforcing agents include, for example, $TiO_2$; fibers, such as asbestos, carbon fibers, or the like; silicates and silica powders, such as aluminum silicate (mullite), synthetic calcium silicate, zirconium silicate, fumed silica, crystalline silica graphite, natural silica sand, or the like; boron powders such as boron-nitride powder, boron-silicate powders, or the like; alumina; magnesium oxide (magnesia); calcium sulfate (as its anhydride, dihydrate or trihydrate); calcium carbonates such as chalk, limestone, marble, synthetic precipitated calcium carbonates, or the like;

talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix resin, or the like; single crystal fibers or "whiskers" such as silicon carbide, alumina, boron carbide, iron, nickel, copper, or the like; glass fibers, (including continuous and chopped fibers), such as E, A, C, ECR, R, S, D, and NE glasses and quartz, or the like; sulfides such as molybdenum sulfide, zinc sulfide or the like; barium compounds such as barium titanate, barium ferrite, barium sulfate, heavy spar, or the like; metals and metal oxides such as particulate or fibrous aluminum, bronze, zinc, copper and nickel or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate hemihydrate or the like; natural fillers and reinforcements, such as wood flour obtained by pulverizing wood, fibrous products such as cellulose, cotton, sisal, jute, starch, cork flour, lignin, ground nut shells, corn, rice grain husks or the like; reinforcing organic fibrous fillers formed from organic polymers capable of forming fibers such as poly(ether ketone), polyimide, polybenzoxazole, poly(phenylene sulfide), polyesters, polyethylene, aromatic polyamides, aromatic polyimides, polyetherimides, polytetrafluoroethylene, acrylic resins, poly(vinyl alcohol) or the like; as well as additional fillers and reinforcing agents such as mica, clay, feldspar, flue dust, fillite, quartz, quartzite, perlite, tripoli, diatomaceous earth, carbon black, or the like, or combinations comprising at least one of the foregoing fillers or reinforcing agents.

The fillers and reinforcing agents can be coated with a layer of metallic material to facilitate conductivity, or surface treated with silanes to improve adhesion and dispersion with the polymeric matrix resin. In addition, the reinforcing fillers can be provided in the form of monofilament or multifilament fibers and can be used either alone or in combination with other types of fiber, through, for example, co-weaving or core/sheath, side-by-side, orange-type or matrix and fibril constructions, or by other methods known to one skilled in the art of fiber manufacture. Suitable cowoven structures include, for example, glass fiber-carbon fiber, carbon fiber-aromatic polyimide (aramid) fiber, and aromatic polyimide fiberglass fiber or the like. Fibrous fillers can be supplied in the form of, for example, rovings, woven fibrous reinforcements, such as 0-90 degree fabrics or the like; non-woven fibrous reinforcements such as continuous strand mat, chopped strand mat, tissues, papers and felts or the like; or three-dimensional reinforcements such as braids. Fillers are generally used in amounts of 1 to 50 parts by weight, based on 100 parts by weight of the resin composition.

Suitable heat stabilizer additives include, for example, organo phosphites such as triphenyl phosphite, tris-(2,6-dimethylphenyl)phosphite, tris-(mixed mono- and di-nonylphenyl)phosphite or the like; phosphonates such as dimethylbenzene phosphonate or the like, phosphates such as trimethyl phosphate, or the like, or combinations comprising at least one of the foregoing heat stabilizers. Heat stabilizers are generally used in amounts of 0.01 to 1.0 parts by weight, based on 100 parts by weight of polycarbonate resin and any impact modifier. In one embodiment, the heat stabilizer additive is present in amounts of 0.03 to 0.09 parts by weight, based on 100 parts by weight of the resin composition.

Suitable antioxidant additives include, for example, organophosphites such as tris(nonyl phenyl)phosphite, tris(2,4-di-t-butylphenyl)phosphite, bis(2,4-di-t-butylphenyl)pentaerythritol diphosphite, distearyl pentaerythritol diphosphite or the like; alkylated monophenols or polyphenols; alkylated reaction products of polyphenols with dienes, such as tetrakis[methylene(3,5-di-tert-butyl-4-hydroxyhydrocinnamate)]methane, or the like; butylated reaction products of para-cresol or dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as distearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl)propionate or the like; amides of beta-(3,5-di-tert-butyl-4-hydroxyphenyl)-propionic acid or the like, or combinations comprising at least one of the foregoing antioxidants. Antioxidants are generally used in amounts of 0.001 to 1.0 parts by weight, based on 100 parts by weight of the resin composition.

Suitable light stabilizer additives include, for example, benzotriazoles such as 2-(2-hydroxy-5-methylphenyl)benzotriazole, 2-(2-hydroxy-5-tert-octylphenyl)benzotriazole and 2-hydroxy-4-n-octoxy benzophenone or the like or combinations comprising at least one of the foregoing light stabilizers. Light stabilizers are generally used in amounts of 0.001 to 3.0 parts by weight, based on 100 parts by weight of the resin composition.

Suitable UV absorber additives include for example, hydroxybenzophenones; hydroxybenzotriazoles; hydroxybenzotriazines; cyanoacrylates; oxanilides; benzoxazinones; 2-(2H-benzotriazol-2-yl)-4-(1,1,3,3-tetramethylbutyl)-phenol (CYASORB 5411); 2-hydroxy-4-n-octyloxybenzophenone (CYASORB 531); 2-[4,6-bis(2,4-dimethylphenyl)-1,3,5-triazin-2-yl]-5-(octyloxy)-phenol (CYASORB 1164); 2,2'-(1,4-phenylene)bis(4H-3,1-benzoxazin-4-one) (CYASORB UV-3638); 1,3-bis[(2-cyano-3,3-diphenylacryloyl)oxy]-2,2-bis[[(2-cyano-3,3-diphenylacryloyl)oxy]methyl]propane (UVINUL 3030); 2,2'-(1,4-phenylene)bis(4H-3,1-benzoxazin-4-one); 1,3-bis[(2-cyano-3,3-diphenylacryloyl)oxy]-2,2-bis [[(2-cyano-3,3-diphenylacryloyl)oxy]methyl]propane; nano-size inorganic materials such as titanium oxide, cerium oxide, and zinc oxide, all with particle size less than 100 nanometers; or the like, or combinations comprising at least one of the foregoing UV absorbers. UV absorbers are generally used in amounts of 0.001 to 3.0 parts by weight, based on 100 parts by weight of the resin composition.

Suitable plasticizer additives include, for example, phthalic acid esters such as dioctyl-4,5-epoxy-hexahydrophthalate, tris-(octoxycarbonylethyl)isocyanurate, tristearin, epoxidized soybean oil or the like, or combinations comprising at least one of the foregoing plasticizers. Plasticizers are generally used in amounts of 1 to 50 parts by weight, based on 100 parts by weight of the resin composition.

Suitable antistatic additives include, for example, glycerol monostearate, sodium stearyl sulfonate, sodium dodecylbenzenesulfonate or the like, or combinations of the foregoing antistatic agents. In one embodiment, carbon fibers, carbon nanofibers, carbon nanotubes, carbon black, or any combination of the foregoing can be used in a polymeric resin containing chemical antistatic agents to render the composition electrostatically dissipative. Antistatic agents are generally used in amounts of 0.001 to 5.0 parts by weight, based on 100 parts by weight of the resin composition.

Suitable mold releasing additives include for example, stearyl stearate, pentaerythritol tetrastearate, 1-decene (ethylflo), beeswax, montan wax, paraffin wax, or the like, or combinations comprising at least one of the foregoing mold release agents. Mold releasing agents are generally used in amounts of 0.10 to 3.0 parts by weight, based on 100 parts by weight of the resin composition.

Suitable lubricant additives include for example, fatty acid esters such as alkyl stearyl esters, e.g., methyl stearate or the like; mixtures of methyl stearate and hydrophilic and hydrophobic surfactants comprising polyethylene glycol polymers, polypropylene glycol polymers, and copolymers thereof e.g., methyl stearate and polyethylene-polypropylene glycol copolymers in a suitable solvent; or combinations comprising at least one of the foregoing lubricants. Lubricants are generally used in amounts of 0.01 to 5.0 parts by weight, based on 100 parts by weight of the resin composition.

Suitable pigment additives include for example, inorganic pigments such as metal oxides and mixed metal oxides such as zinc oxide, titanium dioxides, iron oxides or the like; sulfides such as zinc sulfides, or the like; aluminates; sodium sulfo-silicates; sulfates and chromates; carbon blacks; zinc ferrites; ultramarine blue; Pigment Brown 24; Pigment Red 101; Pigment Yellow 119; organic pigments such as azos, di-azos, quinacridones, perylenes, naphthalene tetracarboxylic acids, flavanthrones, isoindolinones, tetrachloroisoindolinones, anthraquinones, anthanthrones, dioxazines, phthalocyanines, and azo lakes; Pigment Blue 60, Pigment Red 122, Pigment Red 149, Pigment Red 177, Pigment Red 179, Pigment Red 202, Pigment Violet 29, Pigment Blue 15, Pigment Green 7, Pigment Yellow 147 and Pigment Yellow 150, or combinations comprising at least one of the foregoing pigments. Pigments are generally used in amounts of 0.00001 to 20 parts by weight, based on 100 parts by weight of the resin composition.

Suitable dyes include, for example, organic dyes such as coumarin 460 (blue), coumarin 6 (green), nile red, or the like; lanthanide complexes; hydrocarbon and substituted hydrocarbon dyes; polycyclic aromatic hydrocarbons; scintillation dyes (for example oxazoles and oxadiazoles); carbocyanine dyes; phthalocyanine dyes; oxazine dyes; carbostyryl dyes; porphyrin dyes; acridine dyes; anthraquinone dyes; arylmethane dyes; azo dyes; diazonium dyes; nitro dyes; quinone imine dyes; tetrazolium dyes; thiazole dyes; perylene dyes, perinone dyes; bis-benzoxazolylthiophene (BBOT); xanthene dyes; fluorophores such as anti-stokes shift dyes which absorb in the near infrared wavelength and emit in the visible wavelength, or the like; luminescent dyes such as 7-amino-4-methylcoumarin; 3-(2'-benzothiazolyl)-7-diethylaminocoumarin; 2-(4-biphenylyl)-5-(4-t-butylphenyl)-1,3,4-oxadiazole; 2,5-bis-(4-biphenylyl)-oxazole; 2,2'-dimethyl-p-quaterphenyl; 2,2-dimethyl-p-terphenyl; 3,5,3"",5""-tetra-t-butyl-p-quinquephenyl; 2,5-diphenylfuran; 2,5-diphenyloxazole; 4,4'-diphenylstilbene; 4-dicyanomethylene-2-methyl-6-(p-dimethylaminostyryl)-4H-pyran; 1,1'-diethyl-2,2'-carbocyanine iodide; 3,3'-diethyl-4,4',5,5'-dibenzothiatricarbocyanine iodide; 7-dimethylamino-1-methyl-4-methoxy-8-azaquinolone-2; 7-dimethylamino-4-methylquinolone-2; 2-(4-(4-dimethylaminophenyl)-1,3-butadienyl)-3-ethylbenzothiazolium perchlorate; 3-diethylamino-7-diethyliminophenoxazonium perchlorate; 2-(1-naphthyl)-5-phenyloxazole; 2,2'-p-phenylen-bis(5-phenyloxazole); rhodamine 700; rhodamine 800; pyrene; chrysene; rubrene; coronene, or the like, or combinations comprising at least one of the foregoing dyes.

Dyes are generally used in amounts of 0.0001 to 20 parts by weight, based on 100 parts by weight of the resin composition.

Where a foam is desired, suitable blowing agents include for example, low boiling halohydrocarbons and those that generate carbon dioxide; blowing agents that are solid at room temperature and when heated to temperatures higher than their decomposition temperature, generate gases such as nitrogen, carbon 25 dioxide ammonia gas, such as azodicarbonamide, metal salts of azodicarbonamide, 4,4' oxybis(benzenesulfonylhydrazide), sodium bicarbonate, ammonium carbonate, or the like, or combinations comprising at least one of the foregoing blowing agents. Blowing agents are generally used in a molar ratio of 2.0 to 10, based on the total moles of structural carbonate units in the polycarbonate, as described in U.S. Pat. No. 5,597,887.

Suitable flame retardant that can be added can be organic compounds that include phosphorus, bromine, and/or chlorine. Non-brominated and non-chlorinated phosphorus-containing flame retardants can be preferred in certain applications for regulatory reasons, for example organic phosphates and organic compounds containing phosphorus-nitrogen bonds.

One type of exemplary organic phosphate is an aromatic phosphate of the formula $(GO)_3P=O$, wherein each G is independently an alkyl, cycloalkyl, aryl, alkaryl, or aralkyl group, provided that at least one G is an aromatic group. Two of the G groups can be joined together to provide a cyclic group, for example, diphenyl pentaerythritol diphosphate, which is described by Axelrod in U.S. Pat. No. 4,154,775. Other suitable aromatic phosphates can be, for example, phenyl bis(dodecyl) phosphate, phenyl bis(neopentyl) phosphate, phenyl bis(3,5,5'-trimethylhexyl) phosphate, ethyl diphenyl phosphate, 2-ethylhexyl di(p-tolyl) phosphate, bis(2-ethylhexyl) p-tolyl phosphate, tritolyl phosphate, bis(2-ethylhexyl) phenyl phosphate, tri(nonylphenyl) phosphate, bis(dodecyl) p-tolyl phosphate, dibutyl phenyl phosphate, 2-chloroethyl diphenyl phosphate, p-tolyl bis(2,5,5'-trimethylhexyl) phosphate, 2-ethylhexyl diphenyl phosphate, or the like. A specific aromatic phosphate is one in which each G is aromatic, for example, triphenyl phosphate, tricresyl phosphate, isopropylated triphenyl phosphate, and the like.

Di- or polyfunctional aromatic phosphorus-containing compounds are also useful, for example, compounds of the formulas below:

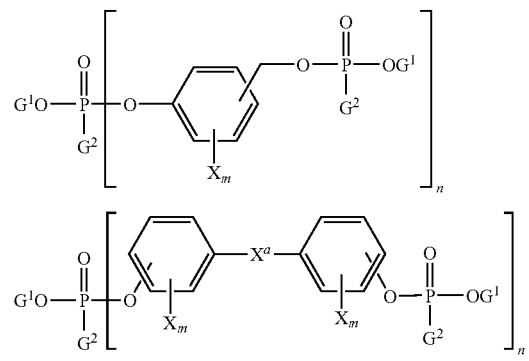

-continued

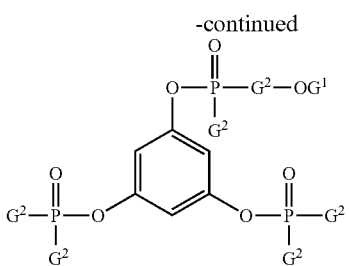

wherein each $G^1$ is independently a hydrocarbon having 1 to 30 carbon atoms; each $G^2$ is independently a hydrocarbon or hydrocarbonoxy having 1 to 30 carbon atoms; each X is independently a bromine or chlorine; m 0 to 4, and n is 1 to 30. Examples of suitable di- or polyfunctional aromatic phosphorus-containing compounds include resorcinol tetraphenyl diphosphate (RDP), the bis(diphenyl) phosphate of hydroquinone and the bis(diphenyl) phosphate of bisphenol-A (, respectively, their oligomeric and polymeric counterparts, and the like. Methods for the preparation of the aforementioned di- or polyfunctional aromatic compounds are described in British Patent No. 2,043,083.

Exemplary suitable flame retardant compounds containing phosphorus-nitrogen bonds include phosphonitrilic chloride, phosphorus ester amides, phosphoric acid amides, phosphonic acid amides, phosphinic acid amides, tris(aziridinyl) phosphine oxide. When present, phosphorus-containing flame retardants can generally be present in amounts of 0.001 to 10 parts by weight, or further can be present in amounts of 0.01 to 5 parts by weight, based on 100 parts by weight of the resin composition.

Halogenated materials are also a useful class of flame retardants. These materials can be aromatic halogen compounds and resins of the formula (15):

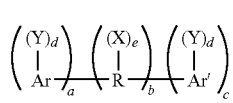 (15)

where R is an alkylene, alkylidene or cycloaliphatic linkage, e.g., methylene, ethylene, propylene, isopropylene, isopropylidene, butylene, isobutylene, amylene, cyclohexylene, cyclopentylidene, or the like; a linkage selected from the group consisting of an oxygen ether; carbonyl; amine; or a sulfur containing linkage, e.g., sulfide, sulfoxide, sulfone, or the like. R can also consist of two or more alkylene or alkylidene linkages connected by such groups as aromatic, amino, ether, carbonyl, sulfide, sulfoxide, sulfone, or the like.

Ar and Ar' in formula (15) are each independently mono- or polycarbocyclic aromatic groups such as phenylene, biphenylene, terphenylene, naphthylene, or the like. Ar and Ar' can be the same or different.

Y is a substituent selected from the group consisting of organic, inorganic, or organometallic radicals. The substituents represented by Y include (1) halogen, e.g., chlorine, bromine, iodine, fluorine or (2) ether groups of the general formula OE, wherein E is a monovalent hydrocarbon radical similar to X or (3) monovalent hydrocarbon groups of the type represented by R or (4) other substituents, e.g., nitro, cyano, and the like, said substituents being essentially inert provided there be at least one and there can be two halogen atoms per aryl nucleus.

When present, each X is independently a monovalent hydrocarbon group, for example an alkyl group such as methyl, ethyl, propyl, isopropyl, butyl, decyl, or the like; an aryl groups such as phenyl, naphthyl, biphenyl, xylyl, tolyl, or the like; and aralkyl group such as benzyl, ethylphenyl, or the like; a cycloaliphatic group such as cyclopentyl, cyclohexyl, or the like. The monovalent hydrocarbon group can itself contain inert substituents.

Each d is independently 1 to a maximum equivalent to the number of replaceable hydrogens substituted on the aromatic rings comprising Ar or Ar'. Each e is independently 0 to a maximum equivalent to the number of replaceable hydrogens on R. Each a, b, and c is independently a whole number, including 0. When b is not 0, neither a nor c can be 0. Otherwise either a or c, but not both, can be 0. Where b is 0, the aromatic groups are joined by a direct carbon-carbon bond.

The hydroxyl and Y substituents on the aromatic groups, Ar and Ar' can be varied in the ortho, meta or para positions on the aromatic rings and the groups can be in any possible geometric relationship with respect to one another.

Included within the scope of the above formula are bisphenols of which the following are representative: 2,2-bis-(3,5-dichlorophenyl)propane; bis-(2-chlorophenyl)-methane; bis(2,6-dibromophenyl)methane; 1,1-bis-(4-iodophenyl) ethane; 1,2-bis-(2,6-dichlorophenyl)ethane; 1,1-bis-(2-chloro-4-iodophenyl)ethane; 1,1-bis-(2-chloro-4-methylphenyl)ethane; 1,1-bis-(3,5-dichlorophenyl)ethane; 2,2-bis-(3-phenyl-4-bromophenyl)ethane; 2,6-bis-(4,6-dichloronaphthyl)propane; 2,2-bis-(2,6-dichlorophenyl)-pentane; 2,2-bis-(3,5-dibromophenyl)hexane; bis-(4-chlorophenyl)phenylmethane; bis-(3,5-dichlorophenyl) cyclohexylmethane; bis-(3-nitro-4-bromophenyl)methane; bis-(4-hydroxy-2,6-dichloro-3-methoxyphenyl)methane; 2,2-bis-(3,5-dichloro-4-hydroxyphenyl)propane; and 2,2 bis-(3-bromo-4-hydroxyphenyl)propane. Also included within the above structural formula are: 1,3-dichlorobenzene, 1,4-dibrombenzene, 1,3-dichloro-4-hydroxybenzene, and biphenyls such as 2,2'-dichlorobiphenyl, polybrominated 1,4-diphenoxybenzene, 2,4'-dibromobiphenyl, and 2,4'-dichlorobiphenyl as well as decabromo diphenyl oxide, and the like.

Also useful are oligomeric and polymeric halogenated aromatic compounds, such as a copolycarbonate of bisphenol A and tetrabromobisphenol A and a carbonate precursor, e.g., phosgene. Metal synergists, e.g., antimony oxide, can also be used with the flame retardant. When present, halogen containing flame retardants can be present in amounts of 0.001 to 10 parts by weight, or can be present in amounts of 0.01 to 5 parts by weight, based on 100 parts by weight of the resin composition.

Inorganic flame retardants can also be used, for example sulfonate salts such as potassium perfluorobutane sulfonate (Rimar salt) and potassium diphenylsulfone sulfonate, as well as the perfluoroalkane sulfonates described in U.S. Pat. No. 3,775,367 or the like; salts formed by reacting for example an alkali metal or alkaline earth metal (which can be lithium, sodium, potassium, magnesium, calcium and barium salts) and an inorganic acid complex salt, for example, an oxoanion, such as alkali metal and alkaline-earth metal salts of carbonic acid, such as $Na_2CO_3$, $K_2CO_3$, $MgCO_3$, $CaCO_3$, $BaCO_3$, and $BaCO_3$ or fluoro-anion complex such as $Li_3AlF_6$, $BaSiF_6$, $KBF_4$, $K_3AlF_6$, $KAlF_4$, $K_2SiF_6$, and/or $Na_3AlF_6$ or the like. When present, inorganic flame retardant salts can generally be present in amounts of 0.001 to 10 parts by weight, and further can be present in amounts of 0.01 to 5 parts by weight, based on 100 parts by weight of the resin composition.

Anti-drip agents may also be used, for example a fibril forming or non-fibril forming fluoropolymer such as polytetrafluoroethylene (PTFE). The anti-drip agent may be encapsulated by a rigid copolymer as described above, for example SAN. PTFE encapsulated in SAN is known as TSAN. Encapsulated fluoropolymers may be made by polymerizing the encapsulating polymer in the presence of the fluoropolymer, for example an aqueous dispersion. TSAN may provide significant advantages over PTFE, in that TSAN may be more readily dispersed in the composition. A suitable TSAN may comprise, for example, 50 wt. % PTFE and 50 wt. % SAN, based on the total weight of the encapsulated fluoropolymer. The SAN may comprise, for example, 75 wt. % styrene and 25 wt. % acrylonitrile based on the total weight of the copolymer. Alternatively, the fluoropolymer may be pre-blended in some manner with a second polymer, such as for, example, an aromatic polycarbonate resin or SAN to form an agglomerated material for use as an anti-drip agent. Either method may be used to produce an encapsulated fluoropolymer. Antidrip agents are generally used in amounts of 0.01 to 20 parts by weight, based on 100 parts by weight of the resin composition.

The relative amounts of each component of the composition will depend on the desired propertied, the particular components used, and the like, and are readily determined by one of ordinary skill in the art using the following guidelines. In one embodiment, the resin composition comprises 4 to 100 wt. % polysiloxane-polycarbonate copolymer, 0 to 15 wt. % impact modifier, and 0 to 96 wt. % additional polymer. In another embodiment, the resin composition comprises 25 to 90 wt. % polysiloxane-polycarbonate copolymer, 0 to 12 wt. % impact modifier, and 10 to 75 wt. % additional polymer preferably a high temperature thermoplastic. In yet another embodiment, the resin composition comprises 30 to 85 wt. % polysiloxane-polycarbonate copolymer, 0 to 10 wt. % impact modifier; and 15 to 70 wt. % of optional additional polymer. All of the foregoing wt. % values are based on the combined weight of the resin composition, that is, the polysiloxane-polycarbonate copolymer, any impact modifier, and any optional additional polymer.

The above-described mixture is thought to be optimal for the performance requirements of a thermally and hydrolytically stable article, in particular an article intended to be steam treated, for example in a dishwasher or an autoclave. A mixture employing lesser amounts of the polysiloxane-polycarbonate copolymer can exhibit a correspondingly lower retention of ductility upon steam treatment, particularly steam sterilization, whereas a mixture employing higher amounts of the polysiloxane-polycarbonate copolymer can exhibit a higher likelihood of delamination or lower resistance to heat-induced deformation which results in softening of the articles over repeated steam treatment.

The compositions can be manufactured by methods generally available in the art, for example, in one embodiment, polysiloxane-polycarbonate copolymer, any impact modifier, any additional polymer, and any optional additives are first blended, optionally with chopped glass strands or other fillers in a Henschel high-speed mixer. Other low shear processes including but not limited to hand mixing can also accomplish this blending. The polysiloxane-polycarbonate copolymer is most effective when it is well dispersed throughout the composition. In some circumstances, mild heating can assist the dispersion of the polysiloxane-polycarbonate copolymer during the mixing operations. Solvents can be used to aid in dispersion of the polysiloxane-polycarbonate copolymer.

The blend may then be fed into the throat of a twin-screw extruder via a hopper. Alternatively, one or more of the components can be incorporated into the composition by feeding directly into the extruder at the throat and/or downstream through a sidestuffer. Additives can also be compounded into a masterbatch with a desired polymeric resin and fed into the extruder. Optionally, it is also possible to include a redistribution catalyst to adjust the molecular weight of the polymers in the blend and/or to effect redistribution of the polysiloxane blocks in the blended. Redistribution catalysts include, for example, catalysts generated by reacting together a branching site generating proportion of a multi-functional phenolic branching agent and a basic transesterification catalyst in the presence of an inert organic solvent. Suitable multi-functional phenolic or carboxylic branching agents useful in reacting with a transesterification catalyst are aromatic and contain at least three functional groups which are carboxyl, carboxylic anhydrides, phenols, haloformyls or mixtures thereof. Some nonlimiting examples of these polyfunctional aromatic compounds include 1,1,1-tri(4-hydroxyphenyl) ethane, 2,2',5,5'-tetra(4-hydroxyphenyl)hexane, trimellitic anhydride, trimellitic acid, trimellitoyl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred multi-functional phenolic or carboxylic compounds are 1,1,1-tri(4-hydroxyphenyl)ethane, trimellitic anhydride, trimellitic acid or their haloformyl derivatives. Suitable transesterification catalysts include, for example, oxides, hydrides, hydroxides, carbonates, carboxylates, alkoxides, or amides of the ammonium, alkylammonium, alkali or alkaline earth metals as well as basic metal oxides such as zinc oxides, salts of weak acids such as lithium stearate and organotitanium, organoaluminums and organotins such as tetraoctyltitanate. Other catalysts include, for example, polyacrylates and polymethacrylates; divinylbenzene; triallylisocyanurate; trimethylolpropane trimethyacrylate; ethoxylated Bisphenol A diacrylate; trimethylolpropane triacrylate; pentaerythritol triacrylate; pentaerythritol tetraacrylate.

The extruder is generally operated at a temperature higher than that necessary to cause the composition to flow. The extrudate is immediately quenched in a water batch and pelletized. The pellets, so prepared, when cutting the extrudate can be one-fourth inch (6.35 mm) long or less as desired. Such pellets can be used for subsequent molding, shaping, or forming.

The composition can also be extruded into films, sheets, tapes, webs, tubes (both cylindrical and non-cylindrical), and the like, or can be shaped, formed or molded, e.g. injection molded, compression molded, or the like, into articles by commercially available and ordinary procedures.

Suitable articles can vary greatly. In one embodiment the article undergoes steam treatment as a regular part of its maintenance and/or use. It is to be understood that "stream treatment" and "contact with steam" as used herein is inclusive of contact with steam alone or steam and water under the indicated conditions. In another embodiment, the article undergoes steam treatment in a steam autoclave ("steam autoclave sterilization") as a regular part of its maintenance and/or use, for example medical devices. Some examples of medical devices are syringes, blood filter housings, blood bags, solution bags, intravenous connectors, dialyzers, catheters, medical storage trays, medical appliances, medical tubing, cardiac pacemakers and defibrillators, cannulas, implantable prostheses, cardiac assist devices, heart valves, vascular grafts, extra-corporeal devices, artificial organs, pacemaker leads, defibrillator leads, blood pumps, balloon pumps, A-V shunts, biosensors, membranes for cell encapsulation, wound dressings, artificial joints, orthopedic implants and syringes.

Examples of non-medical devices that can undergo steam treatment as a regular part of maintenance and/or use include food trays, animal cages, cable sheathings, varnishes and coatings, structural components for pumps and vehicles, mining ore screens and conveyor belts, laminating compounds, aeronautical applications chocolate molds, watercooker components, washer components, dishwasher components, dishwasher safe articles, and the like. In some uses, articles may be subjected to both steam treatment under less rigorous conditions (such as in a dishwasher) and steam autoclave sterilization.

In one specific embodiment, there is provided a method comprising treating an article with steam, wherein at least a portion of the article is formed from a composition comprising an amount of a polysiloxane-polycarbonate copolymer effective to provide thermal and hydrolytic stability to the article for at least 15 cycles, wherein each cycle comprises 20 minutes of contact with steam at 100° C. or greater, at 1.0 atmospheres or greater. In another embodiment, at least a portion of the article is formed from a composition comprising an amount of a polysiloxane-polycarbonate copolymer effective to provide thermal and hydrolytic stability to the article for at least 15 cycles, wherein each cycle comprises 20 minutes of contact with steam at 121° C. or greater, at 1.5 atmospheres or greater.

Another embodiment comprises treating an article with steam, comprising exposing the article to steam for at least 15 cycles at 100° C., and atmospheric pressure, wherein the article comprises a polysiloxane-polycarbonate copolymer in an amount effective to provide thermal and hydrolytic stability to the article. Still another embodiment comprises treating an article with steam, comprising exposing the article to steam for at least 15 cycles at 121° C. and 1.5 atmospheres pressure, wherein the article comprises a polysiloxane-polycarbonate copolymer in an amount effective to provide thermal and hydrolytic stability to the article.

Another embodiment comprises steam autoclaving a medical device, wherein at least a portion of the medical device is formed from a composition comprising an amount of a polysiloxane-polycarbonate copolymer effective to provide autoclave resistance to the article for at least 15 autoclave cycles, wherein each cycle comprises 20 minutes of contact with steam at 121° C. or greater, at 1.5 atmospheres or greater.

In another specific embodiment, there is provided a method of steam sterilizing an article comprising exposing the article to a steam in an for at least 15 cycles at 121° C., 1.5 atmospheres pressure, wherein the article comprises a polysiloxane-polycarbonate copolymer in an amount effective to provide steam autoclave resistance to the article.

Steam sterilization is often used in medical applications due to its expediency and reliability. Steam sterilization can entail autoclaving an article for one or more effective cycles. An effective cycle can vary greatly depending upon the autoclave used, the user of the autoclave and the articles being sterilized, as well as the pressures, temperatures, and cycle length. In addition the autoclave cycle can be conducted in the presence of a variety of steam boiler additives. Typical boiler additives designed to reduce corrosion in steam generating systems are amino compounds such as morpholine, hydrazine, N,N-diethylaminoethanol ("NALCO 359" or "BETZ NA-9"), and octadecylamine. Steam sterilization is also possible in the presence of various hospital cleaners and detergents, such as those sold under the trade names of "Castle 7900" (a sonic cleaner), "Chem Crest 14" (an ultrasonic cleaner), "Tergitol Min Foam 2X" (a non-ionic surfactant), and the like.

In yet another embodiment, the polysiloxane-polycarbonate copolymer is present in an amount sufficient to provide thermal and hydrolytic stability to an article upon treatment with steam for at least 15 cycles at 100° C. under atmospheric pressure, each of 20 minutes duration.

In still another embodiment, the polysiloxane-polycarbonate copolymer is present in an amount sufficient to provide thermal and hydrolytic stability to an article upon steam autoclaving for at least 15 cycles at 121° C., 1.5 atmospheres pressure, each of 20 minutes duration. In another embodiment, the polysiloxane-polycarbonate copolymer is present in an amount sufficient to provide thermal and hydrolytic stability to an article upon steam autoclaving for at least 15 cycles at 121° C., 2.0 atmospheres pressure, each of 20 minutes duration. In still another embodiment, the polysiloxane-polycarbonate copolymer is present in an amount sufficient to provide thermal and hydrolytic stability to the article upon steam autoclaving for at least 15 cycles at 135° C., 1.5 atmospheres pressure, each of 20 minutes duration. In yet another embodiment, the polysiloxane-polycarbonate copolymer is present in an amount sufficient to provide thermal and hydrolytic stability to the article upon steam autoclaving for at least 15 cycles at 135° C., 2 atmospheres pressure, each of 20 minutes duration.

An article with "thermal and hydrolytic stability" as used herein means that following steam treatment, including autoclaving, under the foregoing conditions, an article comprising the inventive compositions does not exhibit a significant decrease in at least one physical or mechanical property such as impact strength, tensile strength, percent ductility, dimensional stability, Vicat softening temperature, transparency, and the like. Steam treatment may occur at 100 to 200° C., under pressures of 1 to 30 atmospheres. A "significant decrease" as used herein means degradation of the particular physical or mechanical property to the extent that it would render the article unfit for future use. It will be appreciated by those skilled in the art that the degradation of a physical property that would render the article unfit for future use can vary greatly depending on factors such as the particular article and the intended use. In the embodiments specified below, various physical and/or mechanical properties of the articles with improved thermal and hydrolytic stability are described. The standard for determining whether a steam treated article can be deemed unfit for future use can be, for example, determining that a syringe after repeated steam sterilization does not meet the property of impact resistance as described below. This standard of fitness for future use can be applied in like fashion to any or all of the physical and/or mechanical properties described below. It will be understood that the steam treatment standard being used herein to determine fitness of future use is only one example of thermal and hydrolytic stability and that equivalent alternative standards for can be determined by those skilled in the art, provided they maintain the parameters of the specific mechanical and/or physical properties of the article following sterilization as described below.

For example, an article having thermal and hydrolytic stability may be capable of withstanding at least 15 treatment cycles wherein each cycle comprises 20 minutes of contact with steam at 100° C., at atmospheric pressure, while retaining at least 50% of its initial tensile strength, specifically at 75% of its initial tensile strength. In another embodiment, an article having thermal and hydrolytic stability may be capable of withstanding at least 15 autoclave cycles where each cycle comprises 20 minutes of contact with steam at 121° C. or 135° C., at 1.5 or 2.0 atmospheres (gauge) pressure, while retaining at least 50% of its initial tensile strength, specifically at 75% of its initial tensile strength.

In another embodiment, an article having thermal and hydrolytic stability may be capable withstanding at least 15 steam treatment cycles wherein each cycle comprises 20 minutes of contact with steam at 100° C. or greater, at atmospheric pressure, while maintaining a percent ductility of 50% to 99%, specifically 60% to 99%, more specifically, 75% to 99%. In another embodiment, an article having thermal and hydrolytic stability may be capable withstanding at least 15 autoclave cycles wherein each cycle comprises 20 minutes of contact with steam at 121° C. or 135° C., at 1.5 or 2.0 atmospheres pressure, while maintaining a percent ductility of 50% to 99%, specifically 60% to 99%, more specifically, 75% to 99%. As used herein, percent ductility may be determined using five to ten one-eighth inch (3.12 mm) ASTM or ISO bars of the subject composition, and subjecting the bars to impact testing per ASTM D 256 or ISO 180/1A, respectively. Generally, stress whitening or a ductile break indicates ductile failure mode, whereas lack of stress whitening or a brittle break indicates brittle failure mode. Percent ductility is expressed as a percentage of bars that exhibited ductile failure mode.

In another embodiment, a significant decrease in dimensional stability means that any dimension of the article changes by more than 10% after at least 15 autoclave cycles where each cycle comprises 20 minutes of contact with steam at 100° C., at atmospheric pressure. In another embodiment, a significant decrease in dimensional stability means that any dimension of the article changes by more than 10% after at least 15 autoclave cycles where each cycle comprises 20 minutes of contact with steam at 121° C. or 135° C., at 1.5 or 2.0 atmospheres (gauge) pressure. For example, when measuring the diameter of unloaded, free tubing both before and after an autoclaving, the dimensions of the tubing diameter at any one point in the tubing should not have changed by more than 10 percent after treatment in steam at 100° C. at atmospheric pressure for the article be considered dimensionally stable. In another embodiment, the dimensions of the tubing at any one point in the tubing should not have changed by more than 5 percent after autoclaving in steam at 121° C. or 135° C., at 1.5 or 2.0 atmospheres after 15 cycles, for the article be considered dimensionally stable.

In another embodiment, an article having thermal and hydrolytic stability may have a Vicat softening temperature (the temperature at which softening of the article is first noticed, as determined by ASTM D-1525) of 121° C. to 400° C., specifically 125° C. to 300° C., and more specifically 130° C. to 220° C., after at least 15 autoclave cycles wherein each cycle comprises 20 minutes of contact with steam at 100° C. at atmospheric pressure. In another embodiment, an article having thermal and hydrolytic stability may have a Vicat softening temperature of 121° C. to 400° C., specifically 125° C. to 300° C., and more specifically 130° C. to 220° C., after at least 15 cycles wherein each cycle comprises 20 minutes of contact with steam at 121° C. or 135° C., at 1.5 or 2.0 atmospheres (gauge) pressure.

In another embodiment, an article having thermal and hydrolytic stability may have a Notched Izod Impact (NII) of 3 to 18 ft-lb/inch (foot pounds per inch), or 3 to 14 ft-lb/inch, measured at room temperature using ⅛-inch (3.12 mm) bars in accordance with ASTM D256, after at least 15 autoclave cycles wherein each cycle comprises 20 minutes of contact with steam at 100° C., at atmospheric pressure. In another embodiment, an article having thermal and hydrolytic stability may have a Notched Izod Impact (NII) of 3 to 18 ft-lb/inch (foot pounds per inch), or 3 to 14 ft-lb/inch, measured at room temperature using ⅛-inch (3.12 mm) bars in accordance with ASTM D256, after at least 15 autoclave cycles wherein each cycle comprises 20 minutes of contact with steam at 121° C. or 135° C., at 1.5 or 2.0 atmospheres (gauge) pressure.

In yet another embodiment, following treatment with steam for at least 15 cycles wherein each cycle comprises 20 minutes of contact with steam at 100° C. at atmospheric pressure, the article can have a percent NII retention of 15% to 100%, specifically 40% to 100%, more specifically 60% to 100%, as determined by ASTM D256. In yet another embodiment, following autoclaving for at least 15 autoclave cycles wherein each cycle comprises 20 minutes of contact with steam at 121° C. or 135° C., at 1.5 or 2.0 atmospheres (gauge) pressure, the article can have a percent NII retention of 15% to 100%, specifically 40% to 100%, more specifically 60% to 100%, as determined by ASTM D256.

The thermoplastic compositions may have significantly improved hydrolytic aging stability, as reflected by a reduction in percent change in weight average molecular weight and/or melt flow after exposure to high humidity conditions. Melt flow is the rate of extrusion of thermoplastics through an orifice at a prescribed temperature and load. It provides a means of measuring flow of a melted material, which can be used to determine the extent of degradation of the plastic as a result of exposure to heat and/or humidity. Degraded materials would generally flow more as a result of reduced molecular weight, and could exhibit reduced physical properties. Typically, melt flow rates are determined before and after storage under conditions of high humidity, then a percentage difference is calculated.

Compositions suitable for the formation of articles may have improved hydrolytic aging stability, in that after 15 treatment cycles of 20 minutes at 100° C., atmospheric pressure, the percent change in melt flow is less than about 20%, specifically less than 1 to 15%, and more specifically less than about 10%, measured in accordance with ISO 1133 at 300° C./1.2 kilogram (Kg) (after six minutes of preheating). Compositions suitable for the formation of autoclavable articles may also have improved hydrolytic aging stability, in that after 15 autoclave cycles of 20 minutes at 121° C. or 135° C., at 1.5 or 2.0 atmospheres (gauge) pressure, the percent change in melt flow is less than about 20%, specifically less than 1 to 15%, and more specifically less than about 10%, measured in accordance with ISO 1133 at 300° C./1.2 kilogram (Kg) (after six minutes of preheating).

Compositions suitable for the formation of articles may have improved hydrolytic aging stability, in that after 15 cycles of 20 minutes at 100° C., atmospheric pressure, the percent change weight average molecular weight is 1 to 10%, or 1 to 8%, or further 1 to 5%, determined by gel permeation chromatography in dichloromethane using polystyrene standards. Compositions suitable for the formation of autoclavable articles may also have improved hydrolytic aging stability, in that after 15 autoclave cycles of 20 minutes at 121° C. or 135° C., at 1.5 or 2.0 atmospheres (gauge) pressure, the percent change weight average molecular weight is 1 to 10%, or 1 to 8%, or further 1 to 5%, determined by gel permeation chromatography in dichloromethane using polystyrene standards.

In one embodiment transparent compositions may be used, for example when visualization through or into the articles is important. For instance, in medical applications such as blood and fluid handling devices, it may be important to be able to observe, for example, bubbles, blood clots, foreign matter, and the like, in blood and drain lines. The compositions described herein allow the manufacture of devices having wall thicknesses of up to ¼ inch (6.35 mm) or more can be formed without adversely affecting the transparency. In addition, following steam treatment for at least 15 cycles wherein each cycle comprises 20 minutes of contact with steam at 100° C. or greater, at atmospheric or greater pressure, the article may have a haze of less than 30% and a transmission of greater than 40%, specifically a haze of less than 20% and a transmission of greater than 50%, more specifically a haze of less than 15% and a transmission of greater than 60% as determined in accordance with ASTM D1003. In addition, following autoclaving for at least 15 autoclave cycles wherein each cycle comprises 20 minutes of contact with steam at 121° C. or 135° C., at 1.5 or 2.0 atmospheres (gauge) pressure, the article may have a haze of less than 30% and a transmission of greater than 40%, specifically a haze of less than 20% and a transmission of greater than 50%, more specifically a haze of less than 15% and a transmission of greater than 60% as determined in accordance with ASTM D1003.

In one embodiment the steam treated or sterilized articles described herein can have increased resistance to steam compared to polycarbonate compositions that do not contain a polysiloxane-polycarbonate copolymer. In one embodiment an autoclave resistant article made from a composition comprising a polysiloxane-polycarbonate copolymer is thermally and hydrolytically stable as described above after 1 to 5000 autoclave cycles at 100° C. to 300° C. at 1 to 3 atmospheres pressure, specifically after 5 to 1000 autoclave cycles at 110° C. to 250° C. at 1 to 2 atmospheres pressure, and more specifically after 10 to 100 autoclave cycles at 120° C. to 200° C. at 1 to 1.8 atmospheres pressure. For example, an autoclave resistant article made from a polysiloxane-polycarbonate copolymer can be dimensionally stable for 1 to 5000 autoclave cycles at 100° C. to 300° C. at 1 to 3 atmospheres pressure, or further can be dimensionally stable for 5 to 1000 autoclave cycles at 110° C. to 250° C. at 1 to 2 atmospheres pressure, and still further can be dimensionally stable for 10 to 100 autoclave cycles at 120° C. to 200° C. at 1 to 1.8 atmospheres pressure.

The invention is further illustrated by the following non-limiting examples.

EXAMPLES

The following materials were used in the Examples below:
A: Polycarbonate-polysiloxane copolymer; 3.5 wt. % polydimethylsiloxane, wherein D=45-50.
B: Polycarbonate-polysiloxane copolymer; 5.0 wt. % polydimethylsiloxane wherein D=45-50.
B1: ISO 10993-tested polysiloxane-polycarbonate; 3.5 wt. % polysiloxane, wherein D=45-50.
LEXAN 141: Multi-purpose, medium viscosity BPA polycarbonate
LEXAN 164H: Polycarbonate product with improved hydrolytic stability
HPS6: High viscosity, high molecular weight polycarbonate
4704: High temperature polyphthalyl-BPA carbonate copolymer.

Example 1

Samples of the above polymers were molded into ASTM bars of 0.125-inch (3.2 mm) thickness. The initial notched Izod impact strength was measured in accordance with ASTM D256. The samples were then placed into a saturated steam autoclave, and the autoclave was maintained at 121° C. (250° F.) for the indicated amount of time. The samples were removed, notched, and the notched Izod impact strength of the autoclaved samples was measured. Data are reported as percent retention of the initial notched Izod impact strength. In all cases, five bars of each sample were measured.

A comparison of the notched Izod impact retention for B1 (3.5% polysiloxane product) and selected polycarbonate products is shown in FIG. 1 and Table 1. Table 1 shows the extended 121° C. autoclave effect on notched Izod impact strength (ft-lb/inch) of selected products. The percent ductility indicates what percentage of the samples break in a ductile manner. "Std dev" as used in all of the examples is the standard deviation.

TABLE 1

|  | B1 | HPS6 | 164H | 4704 |
|---|---|---|---|---|
| 0 hr - Avg | 14.747 | 17.597 | 15.944 | 4.960 |
| Std dev | 0.728 | 1.152 | 0.69 | 3.995 |
| % ductile | 100 | 100 | 100 | 0 |
| 5 hr - Avg | 12.702 | 1.972 | 1.296 | 1.609 |
| Std dev | 0.677 | 0.347 | 0.197 | 0.296 |
| % ductile | 100 | 0 | 0 | 0 |
| 10 hr - Avg | 11.535 | 1.625 | 1.237 | 1.074 |
| Std dev | 0.743 | 0.174 | 0.321 | 0.846 |
| % ductile | 100 | 0 | 0 | 0 |
| 20 hr - Avg | 11.809 | 1.660 | 1.260 | 0.577 |
| Std dev | 0.288 | 0.123 | 0.401 | 0.644 |
| % ductile | 100 | 0 | 0 | 0 |
| 25 hr - Avg | 8.163 | 1.429 | 0.941 | 0.626 |
| Std dev | 0.589 | 0.059 | 0.161 | 0.405 |
| % ductile | 80 | 0 | 0 | 0 |
| 30 hr - Avg | 8.981 | 1.603 | 0.912 | 0.457 |
| Std dev | 0.652 | 0.072 | 0.351 | 0.145 |
| % ductile | 80 | 0 | 0 | 0 |

Although the B1 product is less viscous and has lower heat deformation temperature values than 4704 and HPS6, it has better retention of impact properties after extended autoclaving at 121° C. Surprisingly B1 displays a much greater percent ductility then the other comparative samples, over a much longer average autoclaving period.

Example 2

Samples were molded into ISO Izod bars and notched. The initial notched Izod impact strength was measured. The samples were then placed into a saturated steam autoclave, and the autoclave was maintained at 100° C. (212° F.) for the indicated amount of time. The samples were removed and the notched Izod impact strength of the autoclaved samples was measured. Data are reported as percent retention of the initial notched Izod impact strength. In all cases, five bars of each sample were measured.

Table 2 shown the retention of notched Izod impact strength in kilojoules per square meter ($kJ/m^2$) for polysiloxane-polycarbonate products vs. polycarbonate products. MVR, as used in all of the examples, is the melt viscosity rate expressed in $cm^3/10$ min measured according to ISO 1133. Notched Izod impact strength is given in $kJ/m^2$ according to ISO 180/1A.

TABLE 2

| Composition | | 164H (0% PDMS) | A (5% PDMS) | B (3.5% PDMS) |
|---|---|---|---|---|
| Melt viscosity rate (ISO 1133) | | | | |
| MVR 300° C./1.2 kg-Avg | cm³/10 min | 9.11 | 8.1 | 8.25 |
| MVR-Std dev | cm³/10 min | 0.08 | 0.04 | 0.03 |
| Autoclaving at 100° C.-Izod Notched Impact 23° C. (ISO 180/1A) | | | | |
| 0 hr - Avg | kJ/m² | 73.74 | 54.86 | 59.23 |
| Std dev | kJ/m² | 0.91 | 2.93 | 3.56 |
| % ductile | | 100 | 100 | 100 |
| 25 hrs - Avg | kJ/m² | 7.77 | 41.11 | 49.05 |
| Std dev | kJ/m² | 0.23 | 0.79 | 2.3 |
| % ductile | | 0 | 100 | 100 |
| 50 hrs - Avg | kJ/m² | 6.6 | 33.34 | 42.66 |
| Std dev | kJ/m² | 1.51 | 1.1 | 1.2 |
| % ductile | | 0 | 100 | 100 |
| 100 hrs - Avg | kJ/m² | 6.46 | 29.98 | 38.16 |
| Std dev | kJ/m² | 1.27 | 1.05 | 1.22 |
| % ductile | | 0 | 100 | 100 |
| 200 hrs - Avg | kJ/m² | 6.87 | 22 | 32.38 |
| Std dev | kJ/m² | 0.94 | 1.26 | 1.45 |
| % ductile | | 0 | 20 | 100 |

Figure 2:
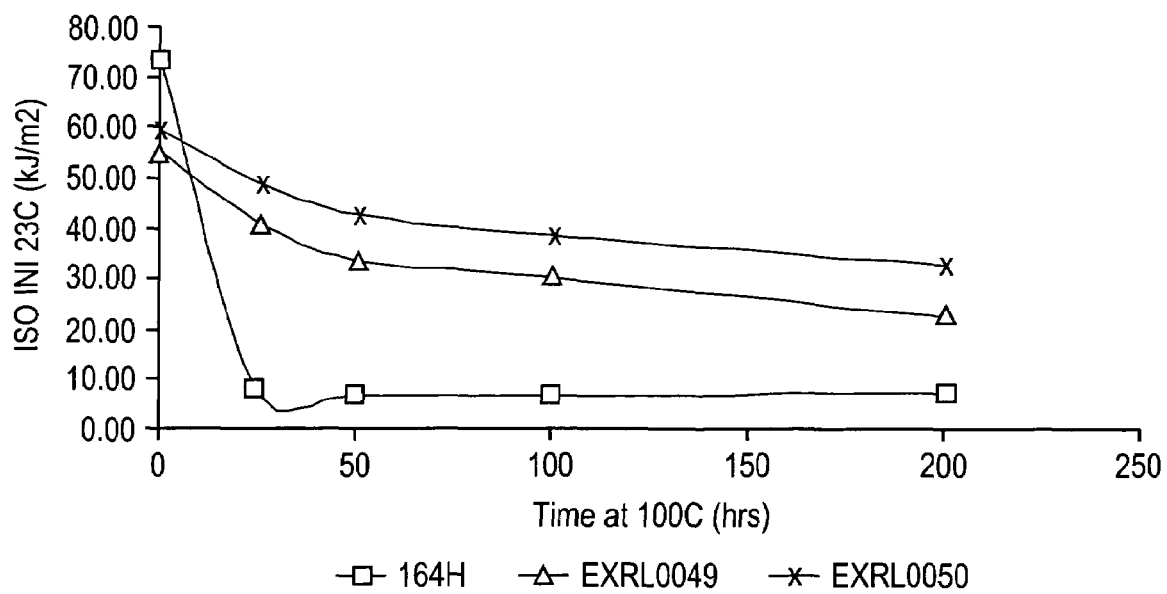
FIG. 2 shows a comparison of notched Izod impact retention for selected polycarbonate compositions after steam treatment.
Figure 3:
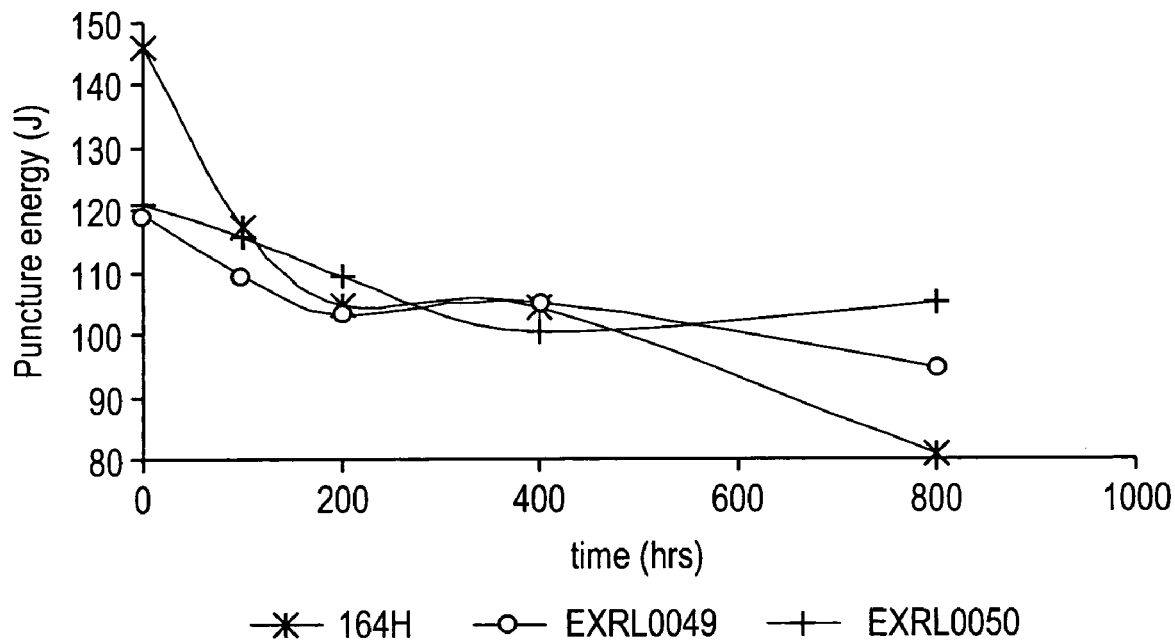
FIG. 3 shows instrumented impact retention values for selected polycarbonate compositions after steam treatment.

The polysiloxane-containing polycarbonate products also show improved property retention at 100° C. (212° F.) and increased pressure. The polysiloxane-containing products A and B show better retention of notched Izod impact and instrumented impact than 164H, a polycarbonate product that is optimized for improved hydrolytic stability as shown in Tables 2 and 3 and FIGS. 2 and 3.

The content of Si (PDMS) indicates the content of silicon in the polydimethylsiloxane. As shown the samples A and B display a maintenance of percent ductility over an extended period of time as opposed to 164H, which has no percent ductility after twenty five hours of autoclaving.

Table 3 shows the retention of instrumented impact energy (J) for polysiloxane-polycarbonate products versus polycarbonate products. Over a period of 800 hours, A and B both retained approximately 85% of their initial energy maximum, while 164H only maintained approximately 56% of its initial energy maximum. Puncture Energy and Energy at the max is expressed in Joules, in accordance with the ISO 6603 method. Ductility is percent ductility as determined by the number of samples that break in a ductile manner.

TABLE 3

| | | 164H | A | B |
|---|---|---|---|---|
| Composition | | | | |
| Content Si (PDMS) | % | 0 | 5 | 3.5 |
| Melt viscosity rate (ISO 1133) | | | | |
| MVR 300 C./1.2 kg-Avg. | cm³/10 min | 9.11 | 8.1 | 8.25 |
| MVR Std. dev. | cm³/10 min | 0.08 | 0.04 | 0.03 |
| ISO flex Plate after 100° C. (J, ISO 6603) | | | | |
| 0 Hrs | Punct energy | 146.2 | 119.5 | 120.9 |
| | Std dev | 8.3 | 7.5 | 1.6 |
| | Energy@max | 120.5 | 90.0 | 94.0 |
| | Std dev | 7.7 | 2.3 | 4.8 |
| | Ductility | 100 | 100 | 100 |
| 100 Hrs | Punct energy | 117.4 | 109.4 | 115.9 |
| | Std dev | 10.7 | 6.9 | 7.8 |
| | Energy@max | 107.7 | 87.9 | 91.1 |
| | Std dev | 8.7 | 5.7 | 5.1 |
| | Ductility | 100 | 100 | 100 |
| 200 Hrs | Punct energy | 104.7 | 103.0 | 109.5 |
| | Std dev | 15.1 | 2.5 | 9.4 |
| | Energy@max | 91.1 | 85.0 | 89.4 |
| | Std dev | 14.6 | 3.6 | 3.4 |
| | Ductility | 80 | 100 | 100 |
| 400 Hrs | Punct energy | 104.5 | 105.2 | 100.5 |
| | Std dev | 11.1 | 6.1 | 9.1 |
| | Energy@max | 89.9 | 82.7 | 83.0 |
| | Std dev | 10.5 | 6.4 | 6.5 |
| | Ductility | 100 | 100 | 100 |
| 800 Hrs | Punct energy | 80.6 | 94.7 | 105.1 |
| | Std dev | 26.4 | 5.1 | 3.8 |
| | Energy@max | 68.0 | 77.1 | 80.9 |
| | Std dev | 24.1 | 3.5 | 2.8 |
| | Ductility | 80 | 100 | 100 |

Example 3

In Example 3 the samples were molded into ASTM Izod bars of 0.125-inch (3.2 mm) thickness. The initial notched Izod impact strength was measured. The samples were then placed into a saturated steam autoclave, and the autoclave was maintained at 121° C. (250° F.) for the indicated amount of time. The samples were removed, notched, and the notched Izod impact strength of the autoclaved samples was measured. Data are reported as percent retention of the initial notched Izod impact strength. In all cases, five bars of each sample were measured.

Table 4 shows the improvement of Notched Izod Impact (ft-lb/in) retention after autoclaving at 121° C. and 1.5 atmospheres by increasing polysiloxane-polycarbonate content.

TABLE 4

| Composition | 4504 | EXL I | EXL II | EXL III |
|---|---|---|---|---|
| % polyphthalyl carbonate | 60 | 60 | 60 | 60 |
| % polycarbonate | 40 | 20 | 20 | 0 |
| % polysiloxane-polycarbonate | 0 | 20 | 20 | 40 |
| Melt Flow Rate (g/cm³) | 3.06 | 4.02 | 3.35 | 3.77 |
| HDT (° C., 1.8 Mpa) | 142.0 | 140.8 | 141.2 | 137.9 |
| Notched Izod Impact (ft-lb/in, ASTM D256) | | | | |
| 0 hr - Avg | 11.427 | 11.502 | 10.893 | 10.643 |
| Std dev | 0.535 | 0.461 | 0.383 | 0.578 |
| % Ductile | 20 | 100 | 100 | 100 |
| 20 hr - Avg | 2.054 | 3.391 | 2.731 | 6.628 |
| Std dev | 0.071 | 0.107 | 0.170 | 2.724 |
| % Ductile | 0 | 0 | 0 | 0 |
| 20 hr - Avg | 2.093 | 3.462 | 2.831 | 6.007 |
| Std dev | 0.108 | 0.341 | 0.310 | 2.957 |
| % Ductile | 0 | 0 | 0 | 0 |

Figure 4:
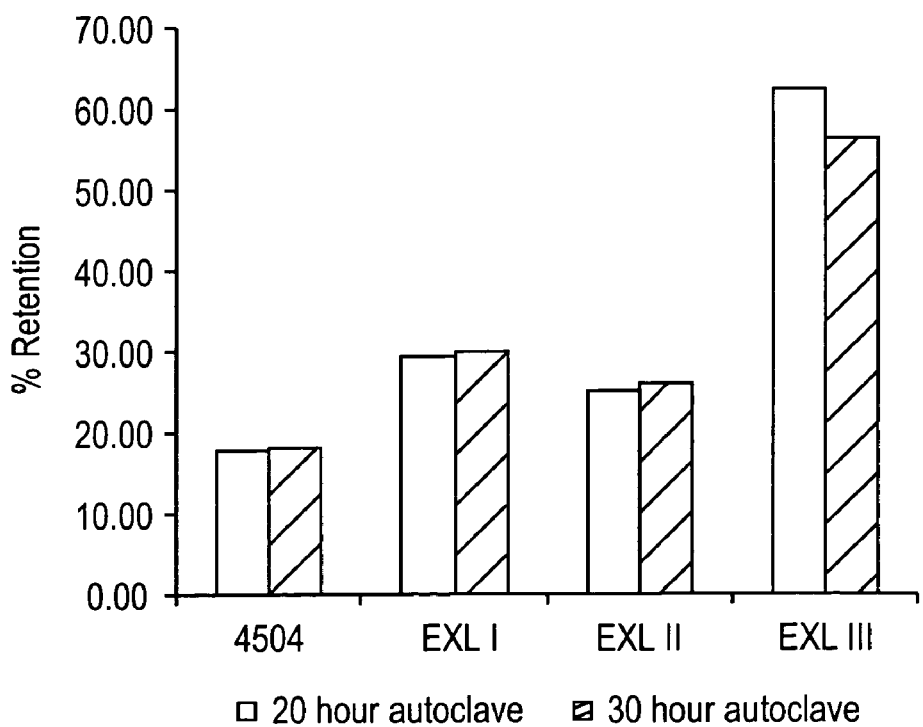
FIG. 4 shows the effect of steam treatment on hydrolytic stability for various polycarbonate compositions.

Blends of BPA-PPC (polyphthalyl carbonate) copolymer, polycarbonate, and polysiloxane-polycarbonate copolymer were subjected to extended autoclave treatment at 121° C. to impart increased hydrolytic stability. The inclusion of the polysiloxane-polycarbonate copolymer increased initial ductility and the retention of Izod impact properties relative to the PPC-PC blend, even though the presence of the polysiloxane reduced the heat distortion temperature of the blend as shown in Table 4 and FIG. 4.

Example 4

In this example 0-100 wt. % a specific high temperature polycarbonate comprising BHPM and BPA units in a weight ratio of 52:48, respectively, were used in a blend with 100-0 wt. % of a polysiloxane-polycarbonate copolymer containing 6% by weight polydimethylsiloxane. The autoclave conditions used in this example are 135° C. and a pressure of 2 bar. The "No. of Cycles" in the table is the number of equivalent cycles of autoclaving for 20 minutes at 135° C. and at a pressure of 2 bar. Notched Izod Impact Strength of the samples is shown in Table 5 below.

vive even 3 autoclave cycles. As can be seen in Table 5 and FIG. 5, the best impact strength performance is in an article that is made of 80% polysiloxane polycarbonate copolymer and 20% BHPM polycarbonate copolymer.

Figure 5:
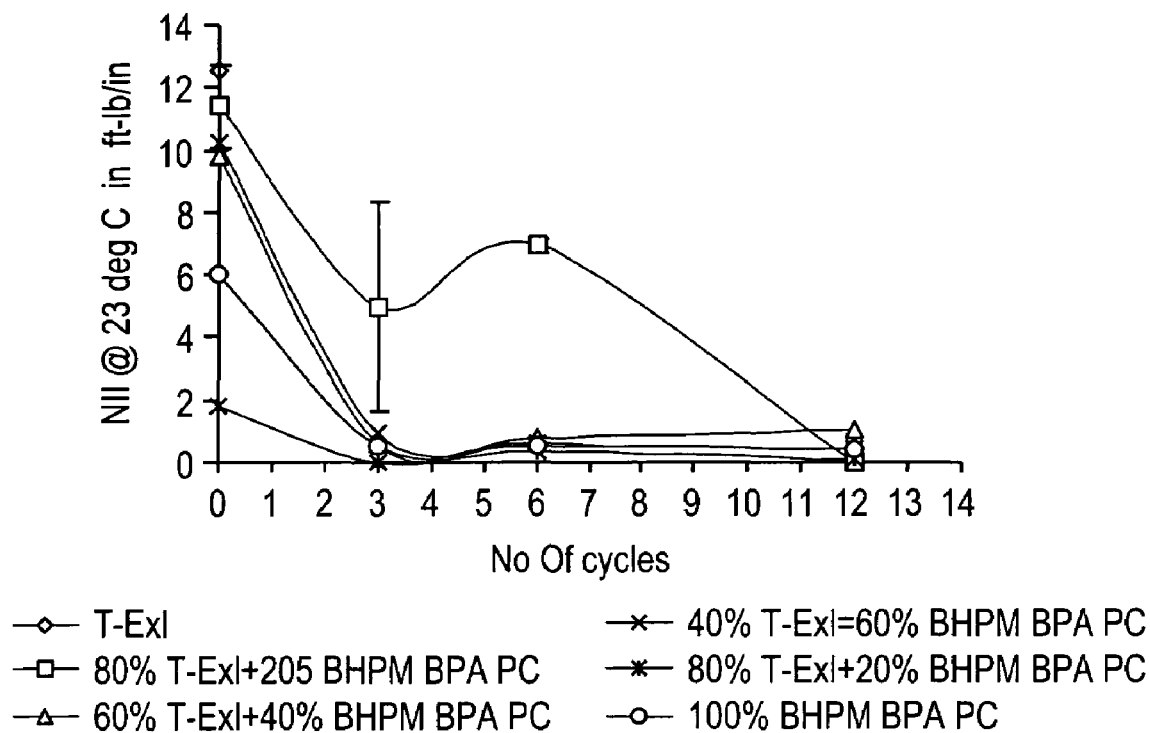
FIG. 5 shows impact strength performance for selected polycarbonate compositions after steam treatment.

As is shown in Table 5 and FIG. 5, samples with lesser amounts of polysiloxane polycarbonate copolymer and greater amounts of BHPM-polycarbonate copolymer show decreased impact strength after only 3 autoclave cycles. Still further, as can be seen from Table 5 and FIG. 5 when 100% of BHPM-polycarbonate copolymer polycarbonate is used, there is a loss of impact strength after only 3 autoclave cycles.

Example 5

Figure 6:
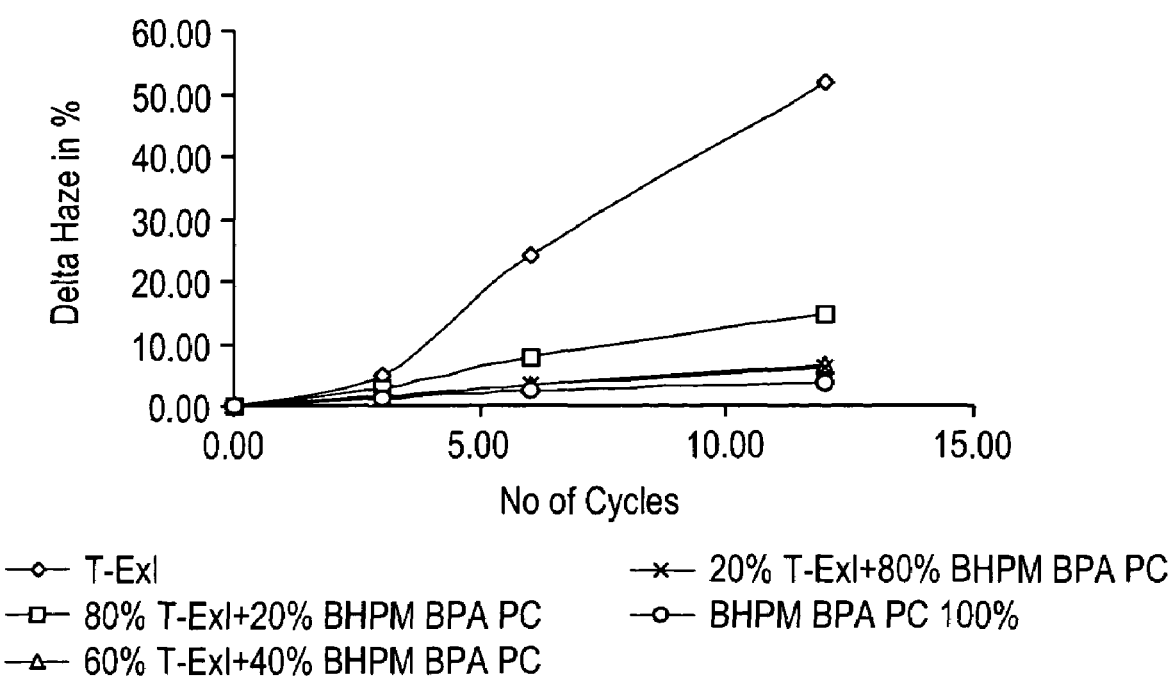
FIG. 6 shows the change in yellowness index ("Delta YI") for selected polycarbonate compositions after steam treatment.

In this example, and as can be seen from Table 6 and FIG. 6, the change in yellowness index ("DeltaYI") of a copolymer of a polysiloxane polycarbonate copolymer described above

TABLE 5

| Weight % polysiloxane-polycarbonate | Weight % BHPM polycarbonate | | | Hours of Autoclaving |  |  |  |
|---|---|---|---|---|---|---|---|
| | | | | 0 | 1 | 2 | 4 |
| | | | | Equivalent Cycles (1 cycle = 20 min) | | | |
| | | | | 0 | 3 | 6 | 12 |
| 100 | 0 | ASTM D256 | avg | 12.51 | Samples Warped | Samples Warped | Samples Warped |
| | | Notched Izod | stdev | 0.2 | | | |
| 80 | 20 | Impact (ftlb/in) | avg | 11.4 | 4.94 | 6.93 | Samples Warped |
| | | | stdev | 1.35 | 3.35 | 0.22 | |
| 60 | 40 | | avg | 9.76 | 0.63 | 0.76 | 1.00 |
| | | | stdev | 1.07 | 0.11 | 0.31 | 0.43 |
| 40 | 60 | | avg | 10.22 | 0.97 | 0.64 | 0.47 |
| | | | stdev | 1.8 | 0.38 | 0.28 | 0.03 |
| 20 | 80 | | avg | 8.5 | 0.5 | 0.65 | 0.4 |
| | | | stdev | 1.8 | 0.03 | 0.31 | 0.07 |
| 0 | 100 | | avg | 6.03 | 0.51 | 0.48 | 0.44 |
| | | | stdev | 3.53 | 0 | 0.06 | 0.01 |

The example shows that the Notched Izod Impact Strength of an article made from a blend of polysiloxane polycarbonate copolymer and BHPM-polycarbonate copolymer is maintained over 6 autoclave cycles while an article made from 100% polysiloxane polycarbonate copolymer does not survive and BHPM-polycarbonate copolymer (need details on this) is at acceptable levels even after 12 autoclave cycles. Acceptable levels of the DeltaYI percent in this example are less than 20%. An autoclave cycle as used in this example is autoclaving for 20 minutes at 135° C. and at a pressure of 2 bar.

TABLE 6

| Weight % polysiloxane-polycarbonate | Weight % BHPM polycarbonate | | | Hours of Autoclaving | | | |
|---|---|---|---|---|---|---|---|
| | | | | 0 | 1 | 2 | 4 |
| | | | | Equivalent Cycles (1 cycle = 20 min) | | | |
| | | | | 0 | 3 | 6 | 12 |
| 100 | 0 | ASTM D1003 | avg | 2.89 | 7.76 | 27.15 | 54.85 |
| | | Yellowness | stdev | | 0.09 | 0.76 | 0.82 |
| 80 | 20 | Index | avg | 1.42 | 4.42 | 9.02 | 16.18 |
| | | | stdev | | 0.41 | 0.33 | 0.08 |
| 60 | 40 | | avg | 1.35 | 2.70 | 4.65 | 7.93 |
| | | | stdev | | 0.09 | 0.20 | 0.27 |
| 20 | 80 | | avg | 1.44 | 3.01 | 4.72 | 7.56 |
| | | | stdev | | 0.24 | 0.35 | 0.30 |
| 0 | 100 | | avg | 0.99 | 2.16 | 3.27 | 4.79 |
| | | | stdev | | 0.24 | 0.31 | 0.20 |

In contrast, as can be seen from Table 6 and FIG. 6, a sample of 100% polysiloxane polycarbonate copolymer is shown to have an unacceptable haze level after 6 autoclave cycles. Still further, as can be seen in Table 6 and FIG. 6, when 100% of BHPM-polycarbonate copolymer is used the percent haze is better maintained at acceptable levels after 12 autoclave cycles.

The articles comprising the polysiloxane-polycarbonate copolymer can be steam sterilized for extended periods without a loss of hydrolytic and/or dimensional stability. In addition, the articles, despite extended steam sterilization, show little to no impairment of all of the advantageous physical properties of polycarbonate such as ductility, impact strength, impact retention, humidity resistance, transparency, and/or softening temperature.

The singular forms "a", "an", and "the" include plural referents unless the context clearly dictates otherwise. The endpoints of all ranges reciting the same characteristic are combinable and inclusive of the recited endpoint. All references are incorporated herein by reference.

While the invention has been described with reference to a specific embodiment, it will be understood by those skilled in the art that various changes can be made and equivalents can be substituted for elements thereof without departing from the scope of the disclosure. In addition, many modifications can be made to adapt a particular situation or material to the teachings of the disclosure without departing from essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A method comprising
treating an article with steam, wherein the article comprises a composition comprising an amount of a polysiloxane-polycarbonate copolymer and a copolyester polycarbonate copolymer effective to provide thermal and hydrolytic stability to the article for at least 15 cycles, wherein each cycle comprises 20 minutes of contact with steam at a temperature of 100° C., at atmospheric pressure wherein the polysiloxane-polycarbonate copolymer consists of units derived from a polycarbonate block and a polydiorganosiloxane block and optionally a chain termination agent wherein the copolyester polycarbonate copolymer comprises repeating structural carbonate units of formula (1):

and repeating structural ester units of formula (6):

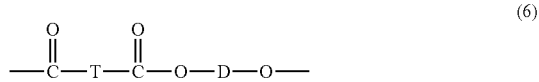

where at least 60 percent of the total number of $R^1$ groups are aromatic organic radicals and the balance thereof are aliphatic, alicyclic or aromatic radicals and D is a divalent radical derived from a dihydroxy compound and T is a divalent radical derived from a dicarboxylic acid.

2. The method of claim 1, wherein the article comprises a composition effective to provide thermal and hydrolytic stability to the article for at least 15 cycles, wherein each cycle comprises 20 minutes of contact with steam at 121° C., at 1.5 atmospheres.

3. The method of claim 1, wherein the article comprises a composition effective to provide thermal and hydrolytic stability to the article for at least 15 cycles, wherein each cycle comprises 20 minutes of contact with steam at 135° C., at 2.0 atmospheres.

4. The method of claim 1 wherein the polysiloxane-polycarbonate copolymer comprises 0.1 to 40 wt. % of polydimethylsiloxane, or an equivalent molar amount of another polydiorganosiloxane.

5. The method of claim 1 wherein the composition comprises 4 to 100 wt. % polysiloxane-polycarbonate copolymer based on the total weight of the resin composition.

6. The method of claim 1 where the composition comprises 1 to 96 wt. % of the copolyester polycarbonate copolymer, wherein the copolymer has a heat deflection temperature at 1.8 Mpa of greater than 135° C. measured per ASTM D 648.

7. The method of claim 1 where the copolyester polycarbonate copolymer comprises units derived from bis(4-hydroxyphenyl)-p-menthane, 2-phenyl, 3-3-bis(4-hydroxylphenyl)phthalimidine, 4,4'-(hexahydro-4,7-methano-indan-5-ylidene)diphenol, bisphenol(1,3,5-trimethylcyclohexane), 4-[1-[3-(4-hydroxyphenyl)-4-methylcyclohexyl]-1-methylethyl]phenol, 4,4'-[1-methyl-4-(1-methylethyl)-1,3-cyclohexandiyl]bisphenol, phenolphthalein, 2-methyl-3,3-bis(p-hydroxyphenyl)phthalimide, 2-butyl-3,3-bis(p-hydroxyphenyl)phthalimide, 2-octyl-3,3-bis(p-hydroxyphenyl)phthalimide, or a combination comprising at least one of the foregoing, and units derived from an aromatic dicarboxylic acid.

8. The method of claim 1 where treating the article with steam is sufficient to accomplish sterilization.

9. The method of claim 8, wherein treating the article with steam occurs in an autoclave.

10. The method of claim 1 wherein the amount of the polysiloxane-polycarbonate copolymer is sufficient to provide the article with a ductility of 50% to 99% after 15 cycles.

11. The method of claim 1 wherein the amount of the polysiloxane-polycarbonate copolymer is sufficient to provide the article with a Vicat softening temperature of 121° C. to 400° C. after 15 cycles.

12. The method of claim 1 wherein the amount of the polysiloxane-polycarbonate copolymer is sufficient to provide the article with a notched Izod impact strength of 3 to 18 foot-lbs/inch as determined by ASTM D256 after 15 autoclave cycles.

13. The method of claim 1 wherein the amount of the polysiloxane-polycarbonate copolymer is sufficient to provide the article with a notched Izod impact retention of 15 to 100% after 15 autoclave cycles, wherein notched Izod impact strength is determined by ASTM D256.

14. The method of claim 1 wherein the amount of the polysiloxane-polycarbonate copolymer is sufficient to provide the article with a change in yellowness index of less than 20% after 15 autoclave cycles.

15. The method of claim 1 wherein the amount of the polysiloxane-polycarbonate copolymer is effective to provide the article with a percent haze of 0 to 20% and a percent transmission of 60% to 100% after 15 autoclave cycles.

16. The method of claim 1 wherein the amount of the polysiloxane-polycarbonate copolymer is effective to provide the article with change in any single dimension of less than 10% after 15 autoclave cycles.

17. The method of claim 1 where the article is a medical device.

18. The method of claim 17 wherein the medical device is selected from the group consisting of syringes, blood filter housings, blood bags, solution bags, intravenous connectors, dialyzers, catheters, medical storage trays, medical appliances, medical tubing, cardiac pacemakers and defibrillators, cannulas, implantable prostheses, cardiac assist devices, heart valves, vascular grafts, extra-corporeal devices, artificial organs, pacemaker leads, defibrillator leads, blood pumps, balloon pumps, A-V shunts, biosensors, membranes for cell encapsulation, wound dressings, artificial joints, orthopedic implants and syringes.

19. The method of claim 1 wherein the article is a non-medical device.

20. The method of claim 19 wherein the non-medical device is selected from the group consisting of food trays, animal cages, cable sheathings, varnishes and coatings, structural components for pumps and vehicles, mining ore screens and conveyor belts, laminating compounds, aeronautical applications and chocolate molds.

21. A method comprising
treating an article with steam, wherein the article comprises a composition comprising an amount of polysiloxane-polycarbonate copolymer and a copolyester polycarbonate copolymer sufficient to provide the article with a notched Izod impact retention of 15 to 100% after 15 autoclave cycles, wherein notched Izod impact strength is determined by ASTM D256, and wherein each cycle comprises 20 minutes of contact with steam at a temperature of 100° C., at atmospheric pressure wherein the polysiloxane-polycarbonate copolymer consists of units derived from a polycarbonate block and a polydiorganosiloxane block and optionally a chain termination agent wherein the copolyester polycarbonate copolymer comprises repeating structural carbonate units of formula (1):

and repeating structural ester units of formula (6):

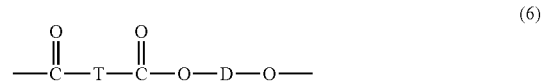

where at least 60 percent of the total number of $R^1$ groups are aromatic organic radicals and the balance thereof are aliphatic, alicyclic or aromatic radicals and D is a divalent radical derived from a dihydroxy compound and T is a divalent radical derived from a dicarboxylic acid.

* * * * *

UNITED STATES PATENT AND TRADEMARK OFFICE
CERTIFICATE OF CORRECTION

PATENT NO. : 7,638,091 B2  Page 1 of 1
APPLICATION NO. : 10/884261
DATED : December 29, 2009
INVENTOR(S) : Chatterjee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 995 days.

Signed and Sealed this

Ninth Day of November, 2010

David J. Kappos
*Director of the United States Patent and Trademark Office*